US007163686B1

(12) United States Patent
Silverman

(10) Patent No.: US 7,163,686 B1
(45) Date of Patent: Jan. 16, 2007

(54) PROTEIN A BASED BINDING DOMAINS WITH DESIRABLE ACTIVITIES

(75) Inventor: Gregg J. Silverman, Encinitas, CA (US)

(73) Assignee: The Regents of the University of California, San Diego, CA (US)

( * ) Notice: Subject to any disclaimer, the term of this patent is extended or adjusted under 35 U.S.C. 154(b) by 0 days.

(21) Appl. No.: 09/979,383

(22) PCT Filed: May 15, 2000

(86) PCT No.: PCT/US00/13402

§ 371 (c)(1),
(2), (4) Date: Apr. 11, 2002

(87) PCT Pub. No.: WO00/69457

PCT Pub. Date: Nov. 23, 2000

Related U.S. Application Data

(60) Provisional application No. 60/134,386, filed on May 15, 1999.

(51) Int. Cl.
*A61K 390/85* (2006.01)
*A61K 45/00* (2006.01)
*A61K 38/00* (2006.01)
*A61K 38/16* (2006.01)
*C07K 14/31* (2006.01)

(52) U.S. Cl. .............................. 424/237.1; 424/282.1; 514/2; 530/350

(58) Field of Classification Search ............. 424/184.1, 424/236.1, 237.1, 243.1, 140.1, 130.1, 93.71, 424/234.1; 514/2; 530/350, 387.1, 300; 604/4.01
See application file for complete search history.

(56) References Cited

U.S. PATENT DOCUMENTS

| 4,879,378 | A |   | 11/1989 | Foster et al. |           |
|-----------|---|---|---------|---------------|-----------|
| 5,100,788 | A |   | 3/1992  | Löfdahl et al.|           |
| 5,189,014 | A | * | 2/1993  | Cowan, Jr. ...................... | 514/2 |
| 5,198,531 | A |   | 3/1993  | Webber et al. |           |
| 5,240,680 | A |   | 8/1993  | Zuckermann et al. |       |
| 5,831,012 | A |   | 11/1998 | Nilsson et al.|           |
| 5,837,500 | A |   | 11/1998 | Ladner et al. |           |
| 5,969,108 | A |   | 10/1999 | McCafferty et al. |       |
| 5,977,322 | A |   | 11/1999 | Marks et al.  |           |
| 5,993,816 | A | * | 11/1999 | Lederman et al. ....... | 424/154.1 |
| 6,013,763 | A |   | 1/2000  | Braisted et al. |         |
| 6,031,071 | A |   | 2/2000  | Mandeville et al. |       |
| 6,060,596 | A |   | 5/2000  | Lerner et al. |           |
| 6,440,418 | B1| * | 8/2002  | Black et al. ............. | 424/154.1 |
| 6,447,777 | B1| * | 9/2002  | Terman et al. ........... | 424/184.1 |

OTHER PUBLICATIONS

Akerstrom, et al., "On the interaction between single chain Fv antibodies and bacterial immunoglobulin-binding proteins," *Journal of Immunological Methods*, 177:151-163 (1994).

Allman, et al., "Peripheral B cell maturation. I. Immature peripheral B cells in adults are heat-stable antigenhi and exhibit unique signaling characteristics." *J. Immunol.*, 149:2533-2540 (1992).

Alting-Mees, et al., "Polycos vectors: a system for packaging filamentous phage and phagemid vectors using lambda phage packaging extracts," *Gene*, 137:93-100 (1993).

Bachmann, et al., "The influence of antigen organization on B cell responsiveness," *Science*, 262:1448-1451 (1993).

Barbas, et al., "In vitro evolution of a neutralizing human antibody to human immunodeficiency virus type 1 to enhance affinity and broaden strain cross-reactivity," *Proc.Natl.Acad.Sci.U.S.A.*, 91:3809-3813 (1994).

Berberian, et al., "A VH clonal deficit in human immunodeficiency virus-positive individuals reflects a B-cell maturational arrest," *Blood*, 78:175-179 (1991).

Berberian, et al., "Immunoglobulin $V_H3$ gene products: natural ligands for HIV gp120," *Science*, 261:1588-1591 (1993).

Boekel, et al., "Precursor B cells showing H chain allelic inclusion display allelic exclusion at the level of pre-B cell receptor surface expression," *Immunity*, 8:199-207 (1998).

Braden, et al., "Anatomy of an antibody molecule: structure, kinetics, thermodynamics and mutational studies of the antilysozyme antibody," D1.3. *Immunol Rev.*, 163:45-57 (1998).

Braisted, et al., "Minimizing a binding domain from protein A," *Proc. Natl. Acad. Sci. USA*, 93:5688-5692 (1996).

Brodeur, et al., "The immunoglobulin heavy chain variable region (Igh-V) locus in the mouse. I. One hundred Igh-V genes comprise seven families of homologous genes," *Eur.J.Immunol.*, 14:922-930 (1984).

Brown, et al., "Specific suppression of the antibody response in vitro by serum from paralyzed mice," *J.Immunol.*, 115:419-424 (1975).

Chothia, et al., "Canonical structures for the hypervariable regions of immunoglobulins," *J. Mol. Biol.*, 196:901-917 (1987).

Cwirla, et al., "Peptides on phage: A vast library of peptides for identifying ligands," *Proc. Natl. Acad. Sci. USA*, 87:6378-6382 (1990).

Demaison, C., "V(H) gene-family representation in peripheral activated B cells from systemic lupus erythematosus (SLE) patients," *Clin.Exp.Immunol.*, 104:439-445 (1996).

(Continued)

*Primary Examiner*—James C Housel
*Assistant Examiner*—Zachariah Lucas
(74) *Attorney, Agent, or Firm*—Foley & Lardner, LLP

(57) ABSTRACT

Provided are Staphylococcal protein A (SpA) variants for binding immunoglobulin (Ig), comprising a polypeptide which varies by one or more amino acids from the amino acid sequence of a natural variable heavy chain III ("VH3") Ig-Fab binding region ("binding region") of SpA, wherein the polypeptide exhibits a different binding specificity for Ig-Fab than does SpA or exhibits a different binding specificity for a non-Ig target molecule than does SpA. Further provided are methods of making the variants and methods of using the variants for in purification of Ig as well as diagnostic and therapeutic intervention.

10 Claims, 9 Drawing Sheets

OTHER PUBLICATIONS

Desaymard, et al., "Rat anti-T15 monoclonal antibodies with specificity for VH- and VH-VL epitopes," *Mol. Immunol.*, 21:961-967 (1984).

Devlin, et al., "Random peptide libraries: A Source of specific protein binding molecules," *Science*, 249:404-406 (1990).

Djojonegoro, et al., "Bacteriophage surface display of an immunoglobulin-binding domain of *Staphylococcus aureus* protein A," *Biotechnology (N. Y.).*, 12:169-172 (1994).

Drew, M.J., "Resolution of refractory, classic thrombotic thrombocytopenic purpura after staphylococcal protein A immunoadsorption," *Transfusion*, 34:536-538 (1994).

Endresen, C., "The binding of protein A of immunoglobulin G and of Fab and Fc fragments," *Acta.path.microbiol.scand., Sect. C*:185-189 (1979).

Feeney, A.J., "Lack of N regions in fetal and neonatal mouse immunoglobulin V-D-J junctional sequences," *J.Exp.Med.*, 172:1377-1390 (1990).

Feeney, A.J., "Predominance of the prototypic T15 antiphosphorylcholine junctional sequence in neonatal pre-B cells," *J. Immunol.*, 147:4343-4350 (1991).

Feijo, et al., "Variable region strucure and Staphylococcal protein A binding specificity of a mouse monoclonal IgM anti-laminin-receptor antibody," *Immunology*, 91:479-485 (1997).

Fields, et al., "Crystal structure of a T-cell receptor beta-chain complexed with a superantigen [see comments]," *Nature*, 384(6605):188-92 (1996).

Goodnow, et al., "Altered immunoglobulin expression and functional silencing of self-reactive B lymphocytes in transgenic mice," *Nature*, 334:676-682 (1988).

Granzow, et al., "Interactions in the fourth dimension," *Bio/Technology*, 10:390 (1992).

Hakoda, et al., "Molecular basis for the interaction between human IgM and staphylococcal protein A," *Clin. Immunol. Immunopathol.*, 72:394-401 (1994).

Hashimoto, et al., "Superantigens and autoantigens may be involved in the pathogenesis of gastric mucosa-associates lymphoid tissue lymphoma," *Int. J Hematol.*, 74(2):197-204 (2001).

Hillson, et al., "The structural basis of germline-encoded $V_H3$ immunoglobulin binding to staphylococcal protein A," *J. Exp. Med.*, 178:331-336 (1993).

Ibrahim, et al., "Proportion of protein A bindable molecules in human IgM and IgA antibodies to seven antigens," *Microb.Pathog.*, 15:159-168 (1993).

Ibrahim, et al., "V-region-mediated binding of human Ig by protein A," *J. Immunol.*, 151:3597-3603 (1993).

Inganas, M., "Comparison of mechanisms of interaction between protein A from *Staphylococcus aureus* and human monoclonal IgG, IgA and IgM in relation to the classical Fc gamma and the alternative F(ab')2 epsilon protein A interactions," *Scand. J. Immunol.* 13:343-352 (1981).

Ito, et al., "A general method for introducing a series of mutations into cloned DNA using the polymerase chain reaction," *Gene*, 102:67-70 (1991).

Jansson, et al., "All individual domains of staphylococcal protein A show Fab binding," *FEMS. Immunol. Med. Microbiol.*, 20:69-78 (1998).

Kabat, et al., "Unusual distributions of amino acids in complementarity-determining (hypervariable) segments of heavy and light chains of immunoglobulins and their possible roles in specificity of antibody-combining sites," *J Biol Chem*, 252(19), 6609-16 (1977).

Kavaler, et al., "A B cell population that dominates the primary response to influenza virus hemagglutinin does not participate in the memory response," *Eur. J. Immunol.*, 21:2687-2695 (1991).

Kirkham, et al., "Immunoglobulin VH clan and family identity predicts variable domain structure and may influence antigen binding," *EMBO J.*, 11:603-609 (1992).

Knappik, et al., "Fully synthetic human combinatorial antibody libraries (huCAL) based on molecular consensus frameworks and CDRs randomized with trinucleotides," *J. Mol. Biol.*, 296:57-86 (2000).

Kotzin, et al., "Superantigens and their potential role in human disease," *Adv Immunol*, 54:99-166. (1993).

Kozlowski, et al., "*Staphylococcus aureus* Cowan I-induced human immunoglobin responses: Preferential IgM rheumatoid factor production and $V_H3$ mRNA expression by protein A-binding B cells," *J. Clin. Immunol.*, 15:145-151 (1995).

Krishnan, et al., "Correlation between the amino acid position of arginine in VH-CDR3 and specificity for native DNA among autoimmune antibodies," *J. Immunol.*, 157:2430-2439 (1996).

Kristiansen, et al., "Staphylococcal protein A induces biased production of Ig by $V_h3$-expressing B lymphocytes," *J. Immunol.*, 153:2974-2984 (1994).

Kushwaha, et al., "Construction and characterization of M13 bacteriophages displaying functional IgG-binding domains of staphylococcal protein A," *Gene*, 151:45-51 (1994).

Lenert, et al., "Ig $V_H$-Dependent Interaction Between Immunoglobulins and CD4," *Intern. Rev. Immunol.*, 14:351-362 (1997).

Li, et al. "The regulated expression of B lineage associated genes during B cell differentiation in bone marrow and fetal liver," *J. Exp. Med.*, 178:951-960 (1993).

Li, et al., "Three-dimensional structure of the complex between a T cell receptor beta chain and the superantigen staphylococcal enterotoxin B," *Immunity*, 9(6):807-16 (1998).

Linton, et al., "Among naive precursor subpopulations only progenitors of memory B cells originate germinal centers," *Eur. J. Immunol.*, 22:1293-1297 (1992).

Maccallum, et al., "Antibody-antigen interactions: contact analysis and binding site topography," *J Mol. Biol.*, 262(5), 732-45 (1996).

Matsuda, et al., "Structure and physical map of 64 variable segments in the 3'0.8 megabase region of the human immunoglobulin heavy-chain locus," *Nature genetics*, 3:88-94 (1993).

Murakami, et al., "Involvement of B-1 cells in mucosal immunity and autoimmunity," *Immunol.Today*, 16:534-539 (1995).

Needleham, et al., "A General method applicable to the search for similarities in the amino acid sequence of two proteins," *J. Mol. Biol.*, 48:443-453 (1970).

Newkirk, et al., "Restricted immunoglobulin variable region gene usage by hybridoma rheumatoid factors from patients with systemic lupus erythematosus and rheumatoid arthritis," *Mol. Immunol.*, 30:255-263 (1993).

Nguyen, et al., "Regulation of anti-DNA B cells in nonautoimmune transgenic mice: Functional and biochemical analyses of self-tolerance," *J. Cell. Biochem.*, 209:Suppl. 18D (1994).

Nord, et al., "A combinatorial library of an alpha-helical bacterial receptor domain," *Protein. Eng.* 8:601-608 (1995).

Nord, et al., "Binding proteins selected from combinatorial libraries of an alpha-helical bacterial receptor domain," *Nat. Biotechnol.*, 15:772-777 (1997).

Olszewski, et al., "Folding Simulations and Computer Redesign of Protein A Trhee-Helix Bundle Motifs," *Proteins: Structure, Function, and Genetics*, 25:286-299 (1996).

Padlan, et al., "Identification of specificity-determining residues in antibodies," *FASEB J*, 9(1):133-9 (1995).

Patten, et al., "Transfer of putative complementarity-determining region loops of T cell receptor V domains confers toxin reactivity but not peptide/MHC specificity," *J Immunol*, 150(6):2281-94 (1993).

Pontzer, et al., "T-cell antigen receptor binding sites for the microbial superantigen staphylococcal enterotoxin A," *Proc. Natl. Acad. Sci. U.S.A.*, 89:7727-7731 (1992).

Pugh-Bernard, et al., "Regulation of inherently autoreactive VH4-34 B cells in the maintenance of human B cell tolerance," *The Journal of Clinical Investigation*, 108(7):1061-1070 (2001).

Pullen, et al., "Analysis of the interaction site for the self superantigen Mls-1a on T cell receptor V beta," *J. Exp. Med.*, 173:1183-1192 (1991).

Randen, et al., "Complementarity-determining region 2 is implicated in the binding of staphylococcal protein A to human immunoglobulin VHIII variable regions," *Eur.J.Immunol.*, 23:2682-2686 (1993).

Riblet, et al., "Genetics of mouse antibodies. I. Linkage of the dextran response locus, VH-DEX, to allotype," *Eur.J.Immunol.*, 5:775-777 (1975).

Roben, et al., "Repertoire cloning of lupus anti-DNA autoantibodies," *J.Clin.Invest.*, 98:2837-2837 (1996).

Roben, et al., "$V_H3$ antibodies bind domain D of staphylococcal protein A[1]," *J.Immunol.*, 154:6437-6446 (1995).

Sankoff, et al., *Time Warps, String Edits, and Macromolecules: The Theory and Practice of Sequence Comparison*, Chapter 1, Addison-Wesley, Reading, Mass. (1983).

Sasano, et al., "Molecular selection of human antibodies with an unconventional bacterial B cell superantigen," *J. Immunol.*, 151:5822-5839 (1993).

Sasso, et al., "Human IgM molecules that bind staphylococcal protein A contain VHIII H chains," *J.Immunol.*, 142:2778-2783 (1989).

Scott, et al., "Searching for peptide ligands with an epitope library," *Science*, 249:386-390 (1990).

Seppala, et al., "Mouse Ig coded by VH families S107 or J606 bind to protein A," *J.Immunol.*, 145:2989-2993 (1990).

Sheriff, et al., "Three-dimensional structure of an antibody-antigen complex," *Proc Natl Acad Sci U S A.*, 84(22), 8075-9 (1987).

Siegel, et al., "Isolation of cell surface-specific human monoclonal antibodies using phage display and magnetically-activated cell sorting: applications in immunohematology," *J.Immunol.Methods*, 206:73-85 (1997).

Silberstein, et al., "Variable region gene analysis of pathologic human autoantibodies to the related i and l red blood cell antigens," *Blood*, 78:2372-2386 (1991).

Silverman, et al., "A B Cell Superantigen-induced Persistent "Hole" in the B-1 Repertoire," *J. Exp. Med.*, 192(1):87-98.

Silverman, et al., "Age-associated changes in binding of human B lymphocytes to a $V_H3$-restricted unconventional bacterial antigen," *J.Immunol.*, 151:5840-5855 (1993).

Silverman, et al., "An endogenous sialoprotein and a bacterial B cell superantigen compete in their VH family-specific binding interactions with human Igs," *J.Immunol.*, 157:4496-4502 (1996).

Silverman, et al., "Distinct patterns of heavy chain variable region subgroup use by human monoclonal autoantibodies of different specificity," *J.Exp. Med.*, 168:2361-2366 (1988).

Silverman, et al., "Neo-self antigens and the expansion of B-1 cells: lessons from atherosclerosis-prone mice," *Curr. Top. Microbiol. Immunol.*, 252:189-200 (2000).

Silverman, et al., "Structural characterization of the second major cross-reactive idiotype group of human rheumatoid factors. Association with the VH4 gene family," *Arthritis Rheum.*, 33:1347-1360 (1990).

Silverman, et al., "Superantigen properties of a human sialoprotein involved in gut-associated immunity," *J.Clin.Invest.*, 96:417-426 (1995).

Silverman, et al., "The dual phases of the response to neonatal exposure to a VH family-restricted staphylococcal B-cell superantigen," *J.Immunol.*, 161:5720-5732 (1998).

Silverman, et al., "The variable-region specificity of bacterial Fab-binding proteins:The search for B cell superantigens," *Immunomethods*, 2:17-23 (1993).

Silverman, G.J., "Adoptive transfer of a superantigen-induced hole in the repertoire of natural IgM-secreting cells," *Cell Immunol.*, 209(1):76-80 (2001).

Silverman, G.J., "B cell superantigens: possible roles in immunodeficiency and autoimmunity," *Immunology*, 10:43-55 (1998).

Silverman, G.J., "Human antibody responses to bacterial antigens: studies of a model conventional antigen and a proposed model B cell superantigen," *Int. Rev. Immunol.*, 9:57-78 (1992).

Silverman, G.J., "Unconventional B-Cell Antigens and Human Immune Repertoires[a]," *Annals of the New York Academy of Sciences*, Sep. 29, 1995, 342-355.

Smith, G.P., "Filamentous fusion phage: novel expression vectors that display cloned antigens on the virion surface," *Science*, 228:1315-1317 (1985).

Starovasnik, et al., "Structural mimicry of a native protein by a minimized binding domain," *Proc.Natl.Acad.Sci.U.S.A.*, 94:10080-10085 (1997).

Taleghani, et al., "Treatment of patients withfactor viii autoantibodies by staphylococcal protein a-based immunoadsorption and immunosuppression," *Br. J. Haematol.*, 114(4):954-962 (2001).

Tighe, et al., "Peripheral deletion of rheumatoid factor B cells after abortive activation by IgG," *Proc.Natl.Acad.Sci.U.S.A.*, 94:646-651 (1997).

Tomlinson, et al., "Human immunoglobulin VH and D segments on chromosomes 15q11.2 and 16p11.2," *Hum.Mol.Genet.*, 3:853-860 (1994).

Warner, et al., "Cholera toxin-sensitive and insensitive signaling via surface Ig," *J.Immunol.*, 143:458-463 (1989).

Webb, et al., "T-cell activation by superantigens," *Curr Opin Immunol.*, 6(3), 467-75 (1994).

White, et al., "Antigen recognition properties of mutant V beta 3+ T cell receptors are consistent with an immunoglobulin-like structure for the receptor," *J.Exp.Med.*, 177:119-125 (1993).

White, et al., "The V beta-specific superantigen staphylococcal enterotoxin B: stimulation of mature T cells and clonal deletion in neonatal mice," *Cell*, 56:27-35 (1989).

Whitmore, et al., "Ig isotype switching in B lymphocytes. The effect of T cell-derived interleukins, cytokines, cholera toxin, and antigen on isotype switch frequency of a cloned B cell lymphoma," *Int. Immunol.*, 3:95-103 (1991).

Wiesenhutter, et al., "Treatment of patients with refractory rheumatoid arthritis with extracorporeal protein A immunoadsorption columns: a pilot trial," *J.Rheumatol.*, 21:804-812 (1994).

Wilson, et al., "Antibody-antigen interactions: new structures and new conformational changes," *Curr Opin Struct Biol*, 4(6):857-867 (1994).

Young, et al., "Staphylococcal protein A binding to the Fab of mouse monoclonal antibodies," *J.Immunol.*, 133:3163-3166 (1984).

Zhang, et al., "Rheumatoid factor specificity of a $V_H3$-encoded antibody is dependent on the heavy chain CDR3 region and is independent of protein A binding," *J Immunol*, 161(5):2284-9 (1998).

Supplementary European Search Report for EP Application No. 00 93 2472.

Graille et al., "Crystal structure of a *Staphylococcus aureus* protein A domain complexed with the Fab fragment of a human IgM antibody: Structural basis for recognition of B-cell receptors and superantigen activity." PNAS, 97:5399-5404, 2000.

* cited by examiner

PROTEIN A BASED BINDING DOMAINS WITH DESIRABLE ACTIVITIES

This appl. Claims benefit of U.S. provisional 60/134,386 filed May 15, 1999.

FIELD OF THE INVENTION

This invention relates to the diagnosis and treatment of inflammatory, immunologic and neoplastic diseases and the preparation of domain variants derived from Staphylococcal protein A for diagnostic and therapeutic intervention of these diseases and generation of variants with other desirable activities.

BACKGROUND OF THE INVENTION

Critical to the diagnosis and treatment of certain inflammatory, hematologic and immune disorders is the preparation of reagents that exhibit binding specificity for defined molecular targets in the immune system. It is of paramount importance when using such reagents therapeutically to avoid the adverse non-specific toxic effects that are associated with many current chemotherapeutic or "immunomodulatory" therapeutic agents.

Antibody reagents have been used extensively for the diagnosis and therapy of immune disorders. In the case of immune B cells and B cell derived leukemias, the immunoglobulin (Ig) molecule displayed on the surface of the B cell provides an attractive target for detection by a specific reagent.

For example, antibodies that bind specifically to the binding site of the Ig molecule (i.e., the idiotype) have been developed as potential therapeutic reagents for disease associated B-cell clones. However, practical concerns, including the possible requirement of tailoring therapies for the specific disease-associated clone of each patient, has tempered enthusiasm for this approach despite evidence from experimental systems of the potential efficacy of this type of targeted therapy. Recently, several pharmaceutical companies have received regulatory approval, and successfully brought to market for the treatment of lymphoma, a recombinant antibody specific for the human B-cell surface marker, CD20. However, this reagent is less than optimal as it appears to non-selectively delete all human mature B cells. Furthermore, although antibody reagents can be readily engineered by genetic manipulation to provide useful binding specificities not readily available in nature, there are high costs associated with producing sufficient quantities of reagent in mammalian expression systems for therapeutic intervention.

Thus, a need exists for methods to produce reagents that are engineered to better target immune cells including β-cell cancers which can be expressed economically in microbial expression systems.

SUMMARY OF THE INVENTION

It therefore is an object of the present invention to provide a more effective approach for diagnosing and treating immune disorders or immune cell cancers by preparing improved targeting reagents that bind to an immunoglobulin (Ig) Fab domain expressed on the cell surface. It is also an object of the present invention to prepare variants of Staphylococcal Protein A that exhibit new and improved binding specificity for an Ig Fab domain.

In accomplishing these and other objectives, there has been provided, in accordance with one aspect of the present invention, a Staphylococcal protein A (SpA) variant for binding immunoglobulin (Ig), comprising a polypeptide which varies by one or more amino acids from the amino acid sequence of a natural variable heavy chain III ("$V_H3$") Ig-Fab binding region ("binding region") of SpA, wherein the polypeptide exhibits a different binding specificity for Ig-Fab than does SpA. The SpA variant polypeptide is prepared for example by a method consisting of he steps of:

a) preparing a library of polypeptides which vary in amino acid sequence from a $V_H3$ Ig-Fab binding region of SpA by one or more amino acids; and b) selecting one or more polypeptides from the library by contacting Ig-Fab with the library, and determining whether said polypeptide possesses a different binding specificity for said Ig-Fab than does SpA.

In another embodiment, the present invention provides an SpA variant, comprising a polypeptide which varies by one or more amino acids from the amino acid sequence of a variable heavy chain III ("$V_H3$") Ig-Fab binding region ("binding region") of Staphylococcal protein A (SpA), wherein the polypeptide exhibits a different binding specificity for a non-Ig target molecule than does SpA. This SpA variant polypeptide is prepared for example by a method consisting of he steps of:

c) preparing a library of polypeptides which vary in amino acid sequence from a $V_H3$ Ig-Fab binding region of SpA by one or more amino acids; and, d) selecting one or more polypeptides from the library by contacting a target molecule with the library, and determining whether said one or more polypeptides possesses a different binding specificity for said target molecule than does SpA.

Further provided is a method for detecting the presence of an Ig-Fab expressing lymphocyte subset in a sample of lymphocytes or detecting the presence of a target molecule expressing biological cell subset in a sample of cells using an SpA variant composition.

In yet another embodiment, the present invention provides a method for reducing the number of Ig-Fab expressing lymphocytes belonging to a certain lymphocyte subset in an individual, in whom the number of lymphocytes belonging to that subset are abnormally elevated, the method comprising administering the SpA variant to the individual, wherein administration of the SpA variant reduces the numbers of targeted in the individual, and wherein said reduction has a beneficial therapeutic effect on the individual's health.

BRIEF DESCRIPTION OF THE DRAWINGS

FIG. 9 is an agarose gel electrophoretic analysis showing synthesis of a variant SpA domain D library. Panel A: Lane 1 shows primary DNA amplification product, Helix½ at approximately 145 bp and lane 2 shows low DNA mass Ladder (GIBCO BRL®). Panel B: Lane 3 shows low molecular mass DNA ladder (GIBCO BRL®) and lane 4 shows secondary DNA amplification product, domain D with Sfi I sites at approximately 237 bp. Analysis was performed on 2% TAE/Agarose gels.

DETAILED DESCRIPTION OF THE INVENTION

Figure 1A:
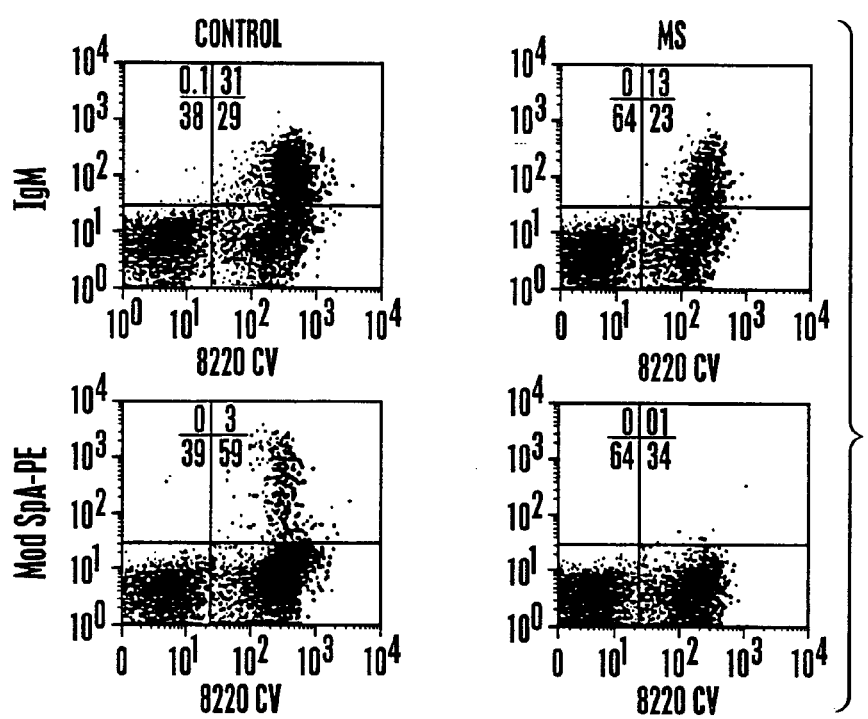
FIG. 1 shows deletion in the peripheral and central compartments of MS-binding B cells following neonatal exposure to MS (mutant form of SpA—MSPA—lacks Fc IgG binding properties). (A) Multiparameter flow cytometric studies were performed on splenocyte suspensions from 15 d old mice following neonatal treatment with MS or a control Ag, OVA. In the control Ag-treated mice, 5.1% of B220+ cells display MS-binding activity, while after MS treatment less than 0.3% of the B220+ cells display MS-binding activity, indicating a selective and near complete loss of detectable MS-binding B cells. (B) Comparable studies from bone marrow suspensions from 15 d old mice following neonatal treatment with MS or a control Ag, OVA, are presented. (C) To ensure that post-treatment changes did not arise from surface modulation of sIgM, findings for the proportion of MS-binding cells among sIgM+ cells are depicted. Following neonatal treatment, the selective loss of MS-binding splenic B cells in MS treated mice (filled circle) was most pronounced at 15 d of age and by 21 d of age was undetectable. Control Ag-treated mice were unaffected (open square). Results representative of four independent experiments of 25 neonatally treated mice, including those depicted in panel A, are displayed. Taken from (68).

The presently disclosed methods for preparing and selecting variants of the superantigen, SpA, which exhibit new or improved binding specificity for an immunoglobulin Fab (Ig-Fab) domain are based upon the inventor's discovery of the critical residues present in SpA domain D that interact with Ig-Fab to mediate the Ig-Fab binding site in SpA. These variant superantigens can be prepared, for example, as libraries expressed using phage-display technology. SpA variants with the appropriate specificity can be selected and further evaluated to determine Fab fine specificity and affinity. Monomers or multimers of the variant domain can be created using, for example, molecular biologic techniques and a bacterial expression system.

SpA Structure and Ig Binding Sites

SpA, which is virulence factor naturally produced by the common bacterial pathogen *Staphylococcus aureus*, exists in both secreted and membrane-associated forms as a 42-kDa protein containing five in tandem highly homologous extracellular immunoglobulin (Ig)-binding domains, designated E, D, A, B and C. Each extracellular domain of SpA possesses distinct Ig-binding sites. One site is for Fcγ (the constant region of IgG class of Ig) and the other is for the Fab portion of certain Ig molecules (the portion of the Ig that is responsible for antigen recognition) (1). The Fcγ binding site has been localized to the elbow region at the CH2 and CH3 interface of most IgG subclasses, and this binding property has been extensively used for the labeling and purification of antibodies (2,3).

The Fab binding site in SpA has previously been less well characterized but was shown to involve a site on the variable region of the Ig heavy chain (4). Each of the five extra-membrane domains of SpA separately contains a Fab-binding site.

Correlation with antibody sequence usage indicates that the Fab targets for the SpA binding site is restricted to Ig encoded by genes from the human $V_H3$ family, which represents nearly half of all inherited VH genes (5–8) and their homologues in other mammalian species (9, 10).

In vitro stimulation of B cells with SpA contributes to selection of these B cells and promotion of antibody production including production of rheumatoid factor (RF) autoantibodies (12, 13), presumably through the interaction of SpA with surface membrane-associated $V_H3$-encoded B-cell antigen receptors (BcR) (11). In contrast, in vivo exposure to recombinant SpA results in supra-clonal suppression and deletion of B lymphocytes that are susceptible based on their VH usage (14, 15). The Fab-binding site of SpA is involved in inducing such a supra-clonal immune deletion or tolerance (or non-responsiveness) in a large sets of β lymphocytes (i.e., acts as a superantigen) through its interaction with surface expressed $V_H3$ family I.

The Ig-Fab binding site in SpA can bind to the Fab portion of about 10–50% of human monoclonal and polyclonal Ig (24–27; 35; 53; 56–59; 65; 70; 73), irrespective of the isotype of H and light (L) chains (28). SpA Fab binding also can detect about 30% of mature B-cells in the circulation of healthy adults as documented in microfluorimetry assays (73). The high frequency of Fab-mediated reactivity with Ig in serum and expressed on cells does not require prior exposure to SpA (28), suggesting that SpA binding results from the inherited V gene sequence expressed in the Ig-Fab domain. Present results indicate that at least 16 and perhaps all of the 22 known potentially functional germline human $V_H3$ gene segments encode a binding site for SpA (57; 55–56).

The inventor has used X-ray crystallographic analysis to define the structural interaction within a resolution of 2.7 Å between a human $V_H3$ Fab of a rheumatoid factor autoantibody and the domain D of staphylococcal protein A. The results show that of the three alpha helices of domain D, binding to Ig Fab primarily resides in helix 2 of domain D, with a smaller contribution from helix 3 of domain D, involving about 1200 Å2 solvent excluded surface. Binding is mediated by a limited set of hydrogen bonds and salt bridges involving only 5 amino acids in the domain D, and stabilized by a large number (greater than 60) of van der Waals interactions.

Notably, the two SpA domain D helices lie across four separate β strands in the $V_H$ region, representing contacts with the FR1-associated B strand, and the FR 3-associated C", D and E strands. Of the 13 identified $V_H$ contact sites, six of these are in these four β strands. The other seven $V_H$ FR contact residues are not specifically in the β strands themselves, but they are still on a face of the $V_H$ region that is remote from the conventional antigen binding pocket (Table I). The $V_H$ contact site resides are highly conserved in all human $V_H3$ gene segments and in many of the $V_H$ gene analogues of more primitive species (discussed further below). The residues in domain D involved in the interaction with Fab are highly conserved in other Ig-binding domains of SpA. This indicates that binding residue predictions from the Fab-domain D interaction disclosed herein also can be applied to SpA variants based on other SpA domains other than domain D so as to prepare and select SpA variants with different binding specificity affinity for Fab or other ligands.

The broad reactivity of SpA with products of the $V_H3$ family is likely in part a reflection of the lack of involvement of CDR loops in Fab-mediated SpA binding.

Crystallographic solution shows that Fab interacts with the helix II and helix III of SpA domain D via a surface composed of four $V_H$ region β-strands: B, C", D and E. The major axis of helix II is positioned approximately 50° from the axial orientation of the $V_H$ region β-strands, and the inter-helical portion of domain D is most proximal to the C" strand. SpA domain D interacts with Fab at a site that is remote from the Ig light chain and the heavy chain constant region. The solution also shows that the SpA domain D interacts with a site that is completely separate from the Ig surfaces involved in the binding a conventional antigen. This explains why antibody binding to conventional antigen does not generally compete with the binding of SpA to the Fab of the antibody (17;90; also for review see 42;49;88;89).

The 2A2 Fab—SpA domain D interaction involves the following domain D residues: Gln26, Gly29, Phe30, Gln32, Ser33 and Asp36 of helix II; Asp37 and Gln40 in the loop between helix II and helix III; and Asn43, Glu47 and Leu51 of helix III. The 2A2 Fab—SpA domain D interaction involves the following Fab heavy chain residues: Gly H15 and Ser H17 in the P turn before strand B; Arg H19 of strand B; Lys H57 and Tyr H59 of strand C; Lys H64, Gly H65 and Arg H66 before strand D; Thr H68 and Ser H70 of strand D; Gln H81 of strand E; Asn H82a and Ser H82b after strand E. Six of the 2A2 heavy chain interacting residues are in framework region (FR) β strands, while the other seven residues are in VH region FR inter-strand loops on the side farthest from the antigen binding pocket.

The results from the crystallographic analysis identifying the SpA residues interacting with 2A2 Fab residues are summarized in Table III. Shown are compiled contacts between the residues in the helix 2, the inter-helical portion, and helix 3 of domain D and the VH region residues in the clan VHIII-encoded 2A2 Fab. In the co-crystal, there are actually two independent domain-D-Fab co-complexes that display similar structural relationships, but for which there are minor differences in the bonds detected. These are indicated separately for each of these non-constrained structures (NCS1 and NCS2) with atomic coordinates deposited in the Protein Data Base, www.rcsb.org (PDB ID Code IDEE).

Overall, the interacting surfaces of Fab and SpA domain D are composed predominantly of polar side-chains, with three negatively charged residues on domain D and two positively charged residues on the 2A2 Fab buried by the interaction, providing an overall electrostatic attraction between the two surfaces. Of the five polar interactions identified between domain D and Fab, three are between side-chains. A salt bridge is formed between Arg H19 and Asp36 and two hydrogen bonds are formed between Tyr H59 and Asp37 and between Asn H82a and Ser33. There also are two hydrogen bonds between main chain atoms and side-chain atoms, namely Gly H15 carbonyl with Gln26, and Lys H57 with Asp36 carbonyl.

A review of all functional human VH genes has been made to determine whether at each VH contact site these specific amino acids would be different in a Fab encoded by the germline configuration product of a human clan VHI or clan VHIII gene. Comparisons of the contact positions in the clan $V_H$III Fab, 2A2, were compared to common VH genes in other clans, and conserved or varied residues in these other clans are indicated (Table IV). Non-conservation variations are underlined. Less common variations are indicated in smaller print. In the clan VHI or clan VHIII vertical rows, the amino acid residues that occur at these sites are indicated in their relative frequency (Table IV).

Table IV identifies domain D codons that could be variegated to generate variant SpA with different binding specificities. If these are non-conservative differences, the amino acid, indicated by the single letter code, is underlined. At many positions the same amino acid is used, and since their spatial position in predicted to be unchanged from 2A2 due to their position in the conserved Ig β stranded barrel structure, it is predicted these interactions would not inherently differ. Therefore, the SpA domain codon relevant to this site would not be randomized in a library designed to enable selection of binders.

These results describing the interaction of Fab with SpA are fundamentally different from the interaction between Fc and SpA. Consequently, approaches to engineering new binding specificities using the Fab and Fc binding sites of SpA have their own set of considerations.

Preparation of Variant SpA

In this invention insights from the experiments and crystallographic analysis disclosed herein are used to design strategies to create SpA variants with different binding specificity for an Ig-Fab domain. As used herein an SpA variant includes one or more domains of SpA that comprise a binding site for an Ig-Fab domain. Domains E, D, A, B and C of SpA are known to contain such binding sites and can be included in the SpA variants prepared herein.

An SpA variant can comprise one or more Ig-Fab domains of SpA and/or multiple copies of a single such domain. For example, variant SpA binding domains can include residues varying from 1–61, 1–59 and 1–58, depending on the domain. An SpA variant can comprise less than a full SpA domain provided such domain includes all amino acid positions that interact with Ig-Fab and all other positions that are necessary to properly position the interacting residues. Variants also include one or more changes in the amino acid positions in an SpA that interact or contact the Fab protein surface. For example, in SpA domain D, residues to vary include one or more of Gly 29, Phe 30, Ser 33, Asp 36, Asp 37 and Val 44. SpA variants that differ at one or more of these positions (in any combination) are preferred herein. Other residues in SpA that can be changed to effect new SpA variants include amino acid residues whose side chains are surface-exposed and close to the surface of the Fab but do not contact the Fab surface. Such potentially interacting residues include, for example, Ala25 of domain D, which does not contact the Fab surface as such but can be changed to another amino acid residue to effect Fab surface contact (or contact with the surface of another target molecule).

SpA variants as described herein also may include conservative substitutions. Conservative substitutions typically include substitutions within chemically related groups of amino acids. For example, aliphatic amino acids glycine and alanine can be substituted while valine, isoleucine, and leucine may be separately substituted. Dicarboxcyclic amino acids, aspartic acid and glutamic acid may be substituted, while amide versions asparagine and glutamine can be substituted. Hydroxyamino acids, serine and threonine can be substituted while basic amino acids, lysine and arginine can be substituted. Also, aromatic amino acids, phenylalanine and tyrosine can be substituted.

Typical homologous SpA variant proteins or peptides will have from 25–100% identity (if gaps can be introduced), to 50–100% identity (if conservative substitutions are included) with the amino acid sequence of the corresponding segment of natural SpA. Sequence identity measures will be at least about 35%, generally at least about 40%, often at least about 50%, typically at least about 60%, usually at least about 70%, preferably at least about 80%, and more preferably at least about 90%. Amino acid sequence homology, or sequence identity, is determined by optimizing residue matches, if necessary, by introducing gaps as required. See also Needleham, et al. (1970) J. Mol. Biol. 48:443–453; Sankoff, et al. (1983) Chapter One in Time Warps, String Edits, and Macromolecules: The Theory and Practice of Sequence Comparison, Addison-Wesley, Reading, Mass.; and software packages from IntelliGenetics, Mountain View, Calif.; and the University of Wisconsin Genetics Computer Group, Madison, Wis.

SpA variants also include derivatives thereof where the protein has been covalently modified by substitution, chemical, enzymatic, or other appropriate means with a moiety other than a naturally occurring amino acid (for example a detectable moiety such as an enzyme or radioisotope).

SpA variants that comprise domain D of SpA are preferred. SpA domain D comprises amino acid residues 1–61 of SpA although smaller segments of domain D including 1–56 and 1–58 also can be used. The SpA variant can include multiple copies of a Fab binding site resulting from multiple copies of an Fab binding site from a single SpA domain and/or a combination of Fab binding sites from more than one SpA domain. An SpA variant also can include Fc IgG binding activity from SpA such that the SpA variant has both the Fc and Fab binding sites. Thus, SpA variants with modified binding sites described herein can be combined with Fc binding sites that are natural or are modified as described in the art. Modifications in the interacting residues or potentially interacting residues of the Fab or the Fc binding sites of SpA can generate an entirely new binding specificity for non Ig molecules.

SpA variants described herein may be synthesized chemically from amino acid precursors for fragments using methods well known in the art, including solid phase peptide synthetic methods such as the Boc (tert-butyloxycarbonyl) or Fmoc (9-fluorenylmethyloxy carbonyl) approaches (see, e.g., U.S. Pat. Nos. 6,060,596; 4,879,378; 5,198,531; 5,240, 680). The amino acid sequence encoding SpA is available from publicly accessible gene banks such as GenBank (see accession number U54636).

SpA variants also can be prepared by genetically engineering DNA encoding the chosen domains or portions thereof of SpA to be included in the variant. A DNA sequence encoding SpA or portion thereof can be synthesized chemically using the known nucleotide sequence of SpA (see, e.g., GenBank accession number E08773 or U54636). A clone encoding SpA also can be obtained from the American Type Culture Collection (ATCC), Rockville Md.

The DNA encoding variant SpA can be cloned into suitable expression vectors for expression by an appropriate host. Vectors are well known in the art and include, for example, cloning vectors and expression vectors that contain the necessary elements for the transcription and translation of the inserted variant SpA coding sequence (see, for example, Goedell, Methods in Enzymology, vol. 185 (Academic Press 1990).

A variety of host-vector systems may be utilized to express the variant SpA-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA, or cosmid DNA. The expression elements of these vectors vary in their productivity and specificity. Depending on the host-vector system utilized, any one of a number of suitable transcription and translation elements may be used.

Variant SpA expression can be accomplished in eukaryotic host cells such as yeasts, insects or mammals, however, expression is preferably accomplished in a bacteria using any of the well known bacterial expression vectors and suitable host cells. Bacterial expression vectors usually comprise a plasmid origin of DNA replication, an antibiotic selectable marker and a promoter and transcriptional terminator separated by a multi-cloning site (expression cassette) and a DNA sequence encoding a ribosome binding site.

The method of transcriptional regulation varies between the various promoters available (e.g., pLac, λpL, T7). The Lac and T7 expression based systems are controlled by the chemical inducer IPTG, while the λ promoters are controlled by a temperature switch.

Variant SpA of the present invention also may be expressed on the surface of a biological particle such as a bacteriophage such that each phage contains a DNA sequence that codes for an individual SpA variant displayed on the phage surface. In this approach, a library of SpA variants are made by synthesizing random or semi random oligonucleotides at selected positions in the SpA sequence chosen to generate a variety of amino acids at these positions. Such variant SpA library contains SpA that have least two different amino acids at one or more amino acid positions compared with the analogous segment of natural SpA.

The encoding DNA is inserted into an appropriate phage vector, packaged into a phage particle and used to infect a suitable bacterial host. Each of the sequences is thus cloned in one phage vector and the SpA variant of interest can be selected by finding those phage that bind to the particular target such as Ig-Fab (by a method known as panning). The phages recovered in this way can be amplified and the selection repeated. Also, the phages can be isolated and the nucleotide sequence encoding selected SpA variants determined by nucleotide sequencing.

The encoding DNA also can be cloned into a phagemid vector which is used to transform a bacterial host. Phage displaying the protein can be obtained by rescue of the phagemid vector from the transformed bacteria with a suitable helper virus. Expression is generally accomplished by inserting the SpA variant encoding DNA into a phage capsid encoding gene such as gene III of filamentous phage. In this way, gene III is expressed as a fusion protein with the variant SpA.

A method for displaying SpA on filamentous phage is described in Examples 9–13. Filamentous phage vectors which are preferred because they do not kill the host. However, phage expression is routine in the art and one can display SpA variants on phage by any number of methods that have been described (see, e.g., U.S. Pat. Nos. 6,031,071; 5,969,108; 5,977,322; 5,837,500 and Knappik et al. J. Mol. Biol. 296:57–86 (2000); Cwirla et al., Proc. Natl. Acad. Sci. USA, 87:6378–6382 (1990); Scott et al., Science, 249: 386–390 (1990); and Devlin et al., Science, 249: 404–406 (1990)).

Selection of Variant SpA

SpA variants of the present invention can be selected from libraries or otherwise tested for binding specificity to the Ig-Fab or another unrelated target molecule. For example, a library of SpA variants displayed on the surface of filamentous phage can be selected for binding to a VH4 family encoded Ig by solid phase panning type approaches well known in the art. Bound phage are then recovered and can be amplified by growth in bacteria. This process can be repeated several times until a highly enriched population of binders is obtained.

The binding specificity of selected SpA variants can also be determined in binding assays well known in the art and described in Example 1. Such assays can be used to characterize the specificity of any new SpA variant with Fab Ig-binding protein activity or other binding activity. One approach is to use these types of in vitro assays to evaluate for possible interactions with different samples of well characterized monoclonal Ig (75). By these comparative assays, using a panel of monoclonal Ig of known V and constant region sequence, one first determines if an interaction is Fc or Fab-specific. As described above, a SAg would be predicted to interact with >5% of a panel of monoclonal Ig from a naïve source, and have preferential binding interactions with the products of certain variable region gene families. Using examples of Ig proteins from all known human and mouse VH families, one can determine whether there is a distinct VH family specificity. Competition assays with known VH specific proteins (i.e. SAgs) would also be performed to investigate whether the same V region sites are being targeted.

Thus, binding assays can be performed using a panel of Ig including those from different VH subfamilies as well as unrelated antigens. SpA variants for which the Fab binding site has been sufficiently modified may be obtained that show greater affinity for Fab or react differently with Fab such that binding to Fab not normally bound by natural SpA can be observed. In addition, variant SpA can be obtained that no longer bind to a Fab but bind to an entirely new target molecule.

The strength of the SpA binding to Ig-Fab can be measured by biosensor studies of real-time kinetics of macromolecular binding (57). Targets for binding can include $V_H3$ Ig such as JGSpA3–08 for IgG Fab, JMSpA3–15 for IgM Fab. The Fab portions of these antibodies are capable of only single point binding interactions with SpA, and demonstrate apparent KD of $1.5\times10^{-7}$ M and $2.1\times10^{-7}$ M for the JGSpA3–08 and JMSpA3–15 Fab, respectively (56). Native $V_H3$ IgM shows significantly stronger binding (>100-fold stronger) presumably due to multivalent binding interactions.

An alternative approach to select variant SpA from a library involves selection based on binding to surface-membrane associated Ig. Hybridomas of diverse VH gene usage already (available from Dr. Tony Marion at the U. of Tennessee)(36)) can be surface biotinylated as described previously (62). A 10-fold cell number of excess unlabelled B-cell hybridoma from clanVHI (e.g. J558) can be added to remove non-specific binding domains. After addition of the library, and washing, specifically bound phage can be isolated using MACS beads (62) that isolate the clanVHIII-associated or other clan V4 family-expressing hybridoma/bound phage.

Utility of SpA Variants

SpA variants prepared by the methods disclosed herein have numerous utilities. For example, SpA variants are useful in diagnostic methods for detecting the presence of a lymphocyte subset that expresses an Ig-Fab. Detection of the lymphocyte subset can be performed by methods well known in the art including flow cytometry and other cell detection methods. Such method also can be adopted to detect the presence of leukemia cells in an individual that expresses the Fab domain that is detected by a particular SpA variant. Thus, an individual can be diagnosed for some forms of leukemia using the SpA variants of the present invention.

Another utility for variant SpA includes in vitro uses for purifying monoclonal or polyclonal antibodies from sera, plasma, tissue culture or other sources. Both naturally occurring antibodies and recombinant antibodies from humans or other species of animal can be purified using variant SpA that show binding specificity to such antibodies. Antibodies purified by these means can be employed in in vitro diagnostic assays and in vivo diagnostic and therapeutic applications.

In addition, SpA variants prepared as described herein also have utility as therapeutic agents. Engineered B-cell superantigens (SAgs) such as SpA variants bind to immunoglobulin receptors on B cells (BCR) in a manner that is distinct from antigen binding by antibody. Superantigen binding to immunoglobulin appears to interact predominantly with a V region surface from only one of the Ig chains, and this does not appear to directly involve the CDR3 loop which is typically involved with antigen recognition.

The direct linkage to specific VH gene segments explains why the binding sites for a superantigen such as SpA are expressed at several orders of magnitude higher frequency than commonly occur for a conventional antigen binding specificity in a naive repertoire. Moreover, because these surfaces are represented in the repertoire at very high frequency solely due to the expression of an inherited V segment, and not because of prior immunologic exposure of the host, superantigen binding interactions have been described as non-immune. Thus, SpA variants having superantigen properties can target a much larger population of Ig expressing B cells in vivo as compared to targeting using a specific antigen.

In the human Ig H chain gene locus, there are an estimated ~50 different functional VH gene segments, and each of these genes has been assigned to one of seven different VH gene families. Genes are assigned to the same family if they possess greater than 80% DNA sequence homology. The greatest conservation of sequence within a family resides in the relatively invariant framework (FR) subdomains.

Further similarities between members of particular VH families allow for clustering of related families into clans.

All known mammalian, amphibian and teleost VH genes can be assigned to one of only three VH clans. When the primary sequences of VH clan members are compared, the greatest amino acid sequence homology is found in the framework (FR) subdomains. In the native folded Ig, most of the amino acid residues in the FR subdomains are used in highly conserved beta strands that maintain the beta barrel structure of the Ig fold.

The Ig beta fold is a structure that has been highly conserved since the first evolutionary appearance of Ig in early chordates. The three dimensional structure of the Fab portion of Ig has been determined for over 100 human and murine antibodies, and most variable region features of secondary structure (i.e. beta barrel) are essential indistinguishable between the two species. Within the framework subdomains the positions of the alpha carbons that contribute to the peptide backbone of these beta strands are essentially identical, except possibly in a few cases in which there are somatic replacement mutations at these sites, an occurrence that is disfavored in vivo. Because the alpha carbon of VH FR1 and FR3 subdomains occupy essentially superimposable positions, even in the products of different VH families, the only predominant structural differences in these subdomains are the side chain atoms that contribute to different framework associated surfaces.

In a Fab, almost all of the FR2 subdomain is folded within the Fab, and hence is not a solvent accessible surface. Due to juxtaposition of their beta strands, the VH FR1 and FR3 subdomains together create a composite surface which presents distinct features that are representative of the products of a VH clan, and which also differ between the products of each of the three VH families and clans.

In the context of microbial B-cell superantigens, the FR1/FR3 encoded VH clan-specific composite surface represents a conserved feature that presents an "achilles heel" which is targeted by these microbial virulence factors to subvert host defenses. SpA variants can be prepared and selected as described herein that target this same achilles heel. Such variants may be selected that exhibit enhanced clan VH3-specific effects in vitro or in vivo such as the ability to delete undesirable B cells that are neoplastic, or which are pathogenic because they are the cellular source of disease-causing autoantibodies.

Therapeutic SpA variants that can bind to Fab on the BcR of an autoreactive B cell or leukemic or lymphoma cell can induce anergy, apoptosis or deletion by other mechanisms. By engineering the interaction between the variant SpA and the Fab as taught herein, one can select for variant SpA that have specially tailored Fab-binding specificities that target pathogenic neoplastic B cell populations (i.e. leukemias or lymphomas), or autoreactive B-cell clones. Therapeutic variant SpA also are useful to treat other conditions that are linked to disease-associated B cells, like idiopathic thrombocytopenia, rheumatoid arthritis, SLE, autoimmune thyroiditis or diabetes among other diseases.

SpA variants also can chemically modified to provide specialized or enhanced therapeutic benefit. For example, the SpA variant can be labeled with a radioisotope or toxin which can enhance killing of the appropriate Ig expressing leukemic cells in a leukemia patient or for killing a particular subset of immune cells. Therapeutic approaches that have been employed for leukemia cell targeting with antibodies also can be applied to targeting of leukemic cells or B cells using the SpA variants of the present invention.

SpA variants to be used in vivo can be prepared by protein synthesis or expressed by genetic engineering methods as is well known in the art. After removal of any contaminating endotoxin, SpA variant preparations can be evaluated for biological efficacy in appropriate superantigen therapy animal models, such adult and neonatal mice or which have monoclonal populations expressing a defined Ig transgene. The effect on the B-cell compartment of administered variant SpA can include measurement of the frequency of spontaneous IgM-secreting cells, the levels of natural antibodies to the variant superantigen, and VH gene family mRNA transcript or Ig protein expression. The efficacy for the induction of supra-clonal B cell deletion also can be measured in (B-cell polyclonal) BALB/c mice, and in transgenic mice that express monoclonal Ig-expressing B cell populations.

SpA variants are administered to an individual in effective amount for treating the individual. An "effective amount" is the amount of the compound that significantly reduces the amount of leukemic cells or B cells in vivo which express the particular Ig-Fab detected by the SpA variant. An range of dosage which achieves an effective amount of the compound described herein for use in humans can be estimated from cell culture assays and animal studies by standard pharmaceutical procedures. For example, the median lethal dose ($LD_{50}$) is the dose lethal to 50% of an experimental animal population and the median effective dose ($ED_{50}$) is the therapeutically effective dose in 50% of the population. The ratio of the $LD_{50}$ to the $ED_{50}$ is a measure of drug safety, known as the therapeutic index. SpA variants which exhibit large therapeutic indices are preferred.

The preferred dosage of a compounds in vivo is usually within a range of circulating concentrations that provide an $ED_{50}$ with little to no toxicity. The dosage may vary within this range depending upon the dosage form employed and the route of administration utilized. Generally, a therapeutically effective amount is achieved by administering between about 0.1 to about 50 mg/kg body weight, depending on a number of factors including, for example, its $EC_{50}$ $IC_{50}$ and on the age, size and condition of the patient.

Numerous modifications may be made to the foregoing systems without departing from the basic teachings thereof. Although the present invention has been described in substantial detail with reference to one or more specific embodiments, those of skill in the art will recognize that changes may be made to the embodiments specifically disclosed in this application, yet these modifications and improvements are within the scope and spirit of the invention as set forth in the claims which follow. All publications, patents, and patent applications cited in this specification are incorporated herein by reference as if each such publication, patent, or patent application was specifically and individually indicated to be incorporated herein by reference.

EXAMPLES

Example 1

Measuring IgG Fc and Fab-Specific Binding Activities of Variant SpA Domains

A variety of dependable in vitro assays are available to evaluate and compare Ig-binding specificities of SpA variants. These include methods for direct and sandwich ELISA, and competitive binding ELISA (57;63;71). Apparent KD can also be determined in an ELISA based method as described previously (57). BIAcore biosensor instrument (Pharmacia) for measurements of surface plasmon resonance (56), for real-time kinetics analysis of Ab-SAg interactions in a label-free mode also have been used previously for SpA. In these studies, SpA derivatives or other SAgs are immobilized on a biosensor chip and the binding of Ig is measured using a direct optical sensing technique based on total internal reflectance. Kinetics software provide binding on and off rates and an accurate characterization of the nature of each interaction (23), as has been recently reported (56;69;71).

Solution phase interactions between Fab and variant SpA also can be measured using ELISA-based inhibition. Results from these solution phase inhibition studies of five forms of SpA are compiled in Table II.

To increase the panel of B cells of defined VH usage for use in selection studies, and for use in analyses of binding specificity, murine B-cell transfectomas using a reported H chain expression vector can be created (78). The mu-loss, κ-expressing variant of the CH12, murine B cell lymphoma line (86) (available from H-M Jaeck, University of Erlangen, Germany), is transfected with a construct of pELVC, which is a highly efficient retroviral-based transfection vector adapted to murine $V_h$-mu expression (78). Cloned VDJ genes (e.g., obtained from Dr. Roy Riblet or available from cloning of RT-PCR studies or RACE libraries of $V_H$ rearrangements) are transferred into the pELVC, which contains a suitable leader sequence, and the membrane exons for VH-mu expression. For this purpose, dozens of $V_H$ genes have been characterized, representing all known major murine $V_H$ families. With available techniques one can directly assess surface Ig binding, or perform affinity/kinetic binding measurements with soluble Ig, An in-frame germline V1-S107 gene has already been transferred into this vector, and will be tested by transformation and expression procedures. The pELVC vector was provided with the 81 X-7183 gene, which will be used in comparisons with other VH genes. Expression will be confirmed by flow cytometric analysis for IgM expression, and S107-linked idiotype expression or by immunoprecipitation studies.

Methods:

Immunogens: As previously described (68;73), endotoxin-free rSpA (Repligen, Cambridge Mass.), or in certain cases aliquots that have been chemically modified to create a form of SpA, termed modified SpA (MspA or MS), that retains VHIII Fab binding specificity but which is devoid of Fc binding activity have been used as the immunogen. Ovalbumin (OVA)(Sigma, St. Louis Mass.), BSA (Sigma), and hen egg lysozyme (HEL) (Sigma) were used as control protein antigens.

Mutagenesis and cloning of domain D' derivatives: To create other recombinant forms of SpA, the pDomD' plasmid that encodes for domain D of SpA (56) was used as template, for application of oligonucleotide-directed site-specific mutagenesis studies (29). With separate pairs of oligonucleotides, the L17D and I31A mutations were created in the plasmid, termed pmDomD', which includes a SpeI site followed by a HindIII site immediately downstream of the mutant domain D' gene. To create concatamers, monomers in pmDomD' were amplified with an oligonucleotide primer that incorporate an upstream NheI site and also adds an interdomain flexible linker paired with the original downstream primer (56). The monomer containing pDomD' plasmid (56) was prepared by digestions at the downstream SpeI and HindIII sites and gel purified, and the special PCR product was digested at the flanking NheI and HindIII sites and purified, and then ligated together to create the dimeric gene plasmid product. To create the four domain product, tetmDomD', the process was repeated two additional times. DNA sequences were determined using an automated sequencer (Applied Biosystems, Foster City, Calif.) with data analysis with the MacVector 4.0 software package (IBI, Rochester, N.Y.). Expression, purification and analysis of DomD' derivatives using the pRSET system (Invitrogen, San Diego, Calif.) has previously been described (56).

Enzyme-linked assays of Ab Response: For inhibition ELISA competition studies, Fab binding values were derived using a representative VHIII-encoded IgG2a Moab that was titered to identify the linear portion of the binding curve. In 100 ul aliquots, SpA forms in solution phase at different concentrations were preincubated with a fixed concentration of this moderate affinity clan VHIII, murine 7183-encoded antibody, for 4 hr at RT, prior to addition to wells coated with tetmDomD' for 1 hr at RT. Saturating levels of human Fc fragments (10 ug/ml) in 1% BSA/BSA were included to remove irrelevant binding from these studies. Plates were then washed, and developed with HRP labeled anti-mouse IgG or IgM, as appropriate. To evaluate for relative Fc binding activity, an assay of similar design was used, except wells were precoated with SpA, and proteins were incubated with a standard concentration of biotinylated-purified IgG Fc fragments (Jackson Labs). After washing, plates were incubated with streptavidin-AP (Kirkegaard and Perry Laboratories, Gaithersburg Md.) at 37° C. for 30 min, then plates developed and read, as described above. Relative inhibition was determined by comparison to a standard curve of the binding protein without inhibitor.

Example 2

Models for Assessing the In Vivo Consequences of B-Cell Superantigen Exposure

The superantigen biological effects of SpA variants can be assessed on human lymphocytes using in vitro preparations of human peripheral blood B cells associated with selective expression of $V_H3$ gene rearrangements (35;37). The in vivo effects of SpA variants can be measured in a mouse animal model (68).

Mice are excellent models for investigations of the in vivo consequences of exposure to a B-cell SAgs, as most aspects of B cell-T cell interactions, and even antigen presentation, are very similar between the human and murine immune systems. Central to these studies, for each of the seven human VH gene segment families, which distribute to each of three VH clans, the mouse also has homologous VH gene segments. In fact, within the 15 known murine VH families, there are at least four murine clan VHIII families, all structurally homologous to human $V_H3$ genes, especially in the FR subdomains, which also usually convey Fab-mediated SpA binding activity (60)(G. Silverman, unpublished observation). While the gene members of the human $V_H3$ family are highly homologous in their FR subdomains, amongst the murine clan VHIII gene analogues there is greater FR⅓ structural diversity. Hence, the murine system provides an opportunity to perform more meaningful comparisons of superantigen binding activity and specificity that should enable the identification of superantigen variants with even broader clanVHIII targeted reactivity. For example, SpA has relatively weak binding activity for most murine VH10 (DNA4)-encoded antibodies, generally moderate activity for VH J606 and 7183-encoded antibodies, and often strongest interactions with the products of the small (3 functional genes in BALB/c) VHS107 gene family (60). In the human system, evidence of a hierarchy of relative Fab-binding affinities for the products of certain clan VHIII gene segments has been found (57).

Example 3

Immunodominance of the Fab-binding Site of SpA: Induction of Tolerance after Neonatal Exposure.

Studies that characterize the outcome of neonatal exposure to MSPA (MS), a chemically modified form of SpA possessing only the clan VHIII-restricted Fab-binding activity have been described (68). MSpA was studied because it is a an oligovalent high avidity Fab-binding form of SpA but it is devoid of the Fc binding activity. In part, these studies addressed the fundamental question of the role of the clan VHIII-restricted Fab binding site for in vivo immune responses to SpA. Within the primary B-cell repertoire of naive adult BALB/c mice, these unconventional BcR-mediated MSPA-binding interactions were detected by flow cytometry for ~5% of splenic B cells, and by ELISpot with ~13% of the splenic spontaneous IgM-secreting cells (68).

The secondary immune responses to MSPA also was evaluated, which occurred in association with antigen-specific T cell responses, and presumably arose from B-2 cells in germinal center reactions. Studies using ELISpot and ELISA demonstrated that, compared to conventional Ag-induced responses (i.e. ovalbumin, OVA; or beta-galactosidase, β-gal), secondary immune IgG responses to MSPA were of >30-fold higher magnitude. Moreover, competition studies with naïve $V_H3$ Ig confirmed that >80% of these induced IgG1 anti-MSPA responses are directed at the Fab-binding site of SpA, documenting its immunodominance. Furthermore, VH family expression by RT-PCR also was surveyed and it was discovered that the secondary responses to MSPA recruited an overwhelming predominance of in the RNA expression of γ1 rearrangment of S107 genes, which have been shown to generally encode for Ig with the highest SpA binding activity (60)(unpublished observation). In contrast, IgG responses to an experimental protein Ag induced expression of γ1 rearrangements from each of the seven VH families evaluated. These data document that the clan VHIII-restricted Fab binding site is dominant during active immune responses, and suggested that S107-encoded antibody responses are selected based on their relative affinity. As discussed below, the SpA/superantigen-induced supra-clonal B cell defect (which may involve deletion of VH targeted extra-follicular B cells) also predominately affects expression of S107-mu rearrangements, which presumably is also due to targeting of B cells with greatest SAg binding activities.

Example 4

In Vivo Exposure to SpA Induces Supra-Clonal B-Cell Deletion

A protocol was used (68) that was previously employed for neonatal treatment with a bacterial T-cell SAg (84), neonatal mice, beginning with 24 hrs of birth, were injected with 100 μg of protein in PBS intraperitoneal every other day for the first two weeks of life (8×100 μg protein) (68). After neonatal MSPA treatment, at day 15 of life there was a near complete loss of detectable MSPA-binding splenic B cells and there were also similar losses of MSPA-binding mature and immature B cell subsets detected in the bone marrow (see FIG. 1). Equivalent studies were also performed with natural SpA in neonatal mice and with proportionally higher doses in adult mice. In vitro incubation of these cells for 24 hr did not alter the representation of MSPA-binding B cells in these SAg-treated mice (unpublished), suggesting that the decreased binding was not due to modulation of surface Ig. These studies provided the first documentation that in vivo exposure to a B-cell SAg can induce supra-clonal deletion in the central and peripheral B-cell compartments. Similar findings would be predicted to occur in response to exposure to a novel SAg with clinically relevant immunologic properties.

Methods:

Microfluorimetric methods for the quantitation of MSPA-specific B cells have recently been described (68). To enumerate the frequency of binding cells in a defined B-cell subset to novel SAgs, flow cytometric studies are performed. These studies are conducted with special concern for the possible effects of cytophilic staining by circulating Ab. SpA domains can be directly labeled with biotin or phycoerythrin, without altering their binding properties (68;73). Using proven methods (68;72), adapted from earlier analysis of human lymphocyte subsets (73), expression of MSPA-binding on cells identified by Abs specific for total T cells (anti-Thy-1: G7), pan B cell (anti-B220: RA3–6B2), B-1 subset marker (anti-Ly-1.1:H11–86.1), and anti-Heat Stable Antigen:M1/69 that identifies B cell subsets that may be memory B cell (41) or a maturation marker (1) was evaluated. B cells are also characterized for surface Ig levels and will be evaluated in both the immediate post-immunization (deletion), and later periods for decreased sIgM phenotype which is a marker for anergic B cells (21;46). A survey for increased expression of the activation markers, MHC class II (82) CD86 (79). In adult mice, less than 8 hours after a single dose of 0.5 mg of SpA, VH clan III splenic B cells specifically upregulate expression of these surface markers B cell activation. As described (72;73), these studies use lymphocyte gating by forward and orthogonal scatter, and propidium iodide to assess cell viability. Studies of blood, spleen and regional lymph nodes have been performed, with peritoneal washings used to study the B-1 (CD5+) repertoire. In most studies, matched groups of 4–8 mice will be used.

Example 5

Suppression of clan VHIII-IGM expression is proportional to Fab binding avidity of the SpA form: There is no correlation with Fc binding activity.

Figure 2A:
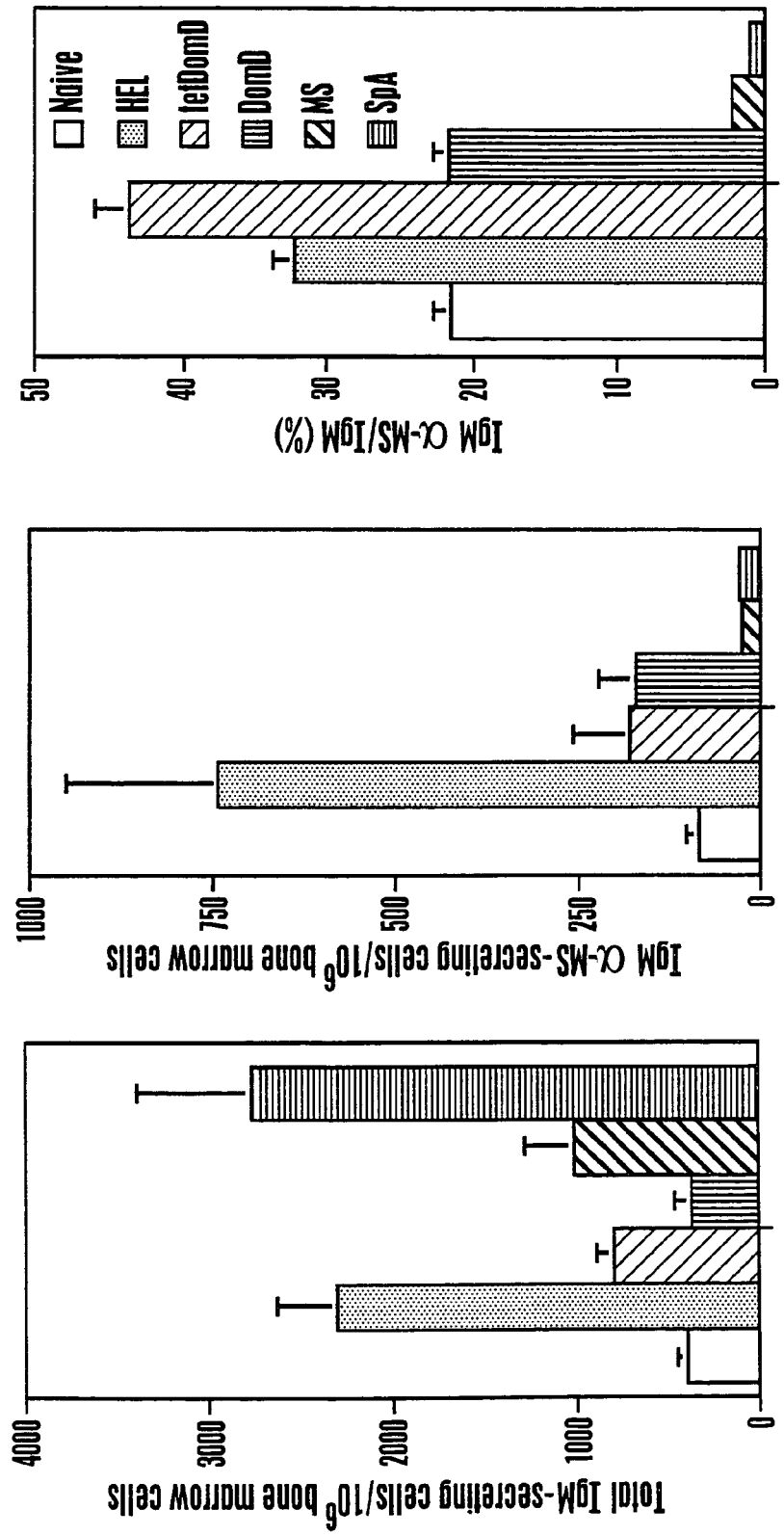
FIGS. 2A and 2B show that treatment with SpA induces persistent loss of surface antigen (SAg)-specific IgM secreting cells in bone marrow and spleen, which is directly proportional to Fab-binding avidity. Neonatal BALB/c mice were treated with different forms of SpA for the first 2 weeks of life, and IgM-secreting cells were quantitated 3–8 months later. Treatment with any protein increases the frequency of total splenic IgM-secreting cells. Control antigens (e.g., HEL hen egg lysozyme, OVA ovalbumin or β-gal) do not alter the proportion (i.e. ~12%) of IgM-secreting cells that are SAg-specific. SpA, the highest avidity form, induces almost complete loss of SAg-specific IgM-secreting cells, while MSPA is a less efficient inhibitor, and monovalent domain D (DomD) induces mild inhibition in the spleen but not in the bone marrow. The weakest Fab-binding form, the tetranumeric mutant form derived of Fc binding activity (tetmDomD'), causes little or no changes. Even more marked effects are demonstrated in the bone marrow. Equivalent changes occur concurrently in circulating Ig levels. Results are from groups of 4–8 mice studied at between 4–6 months of age, using previously described methods (68). Mean±SEM.
Figure 2B:
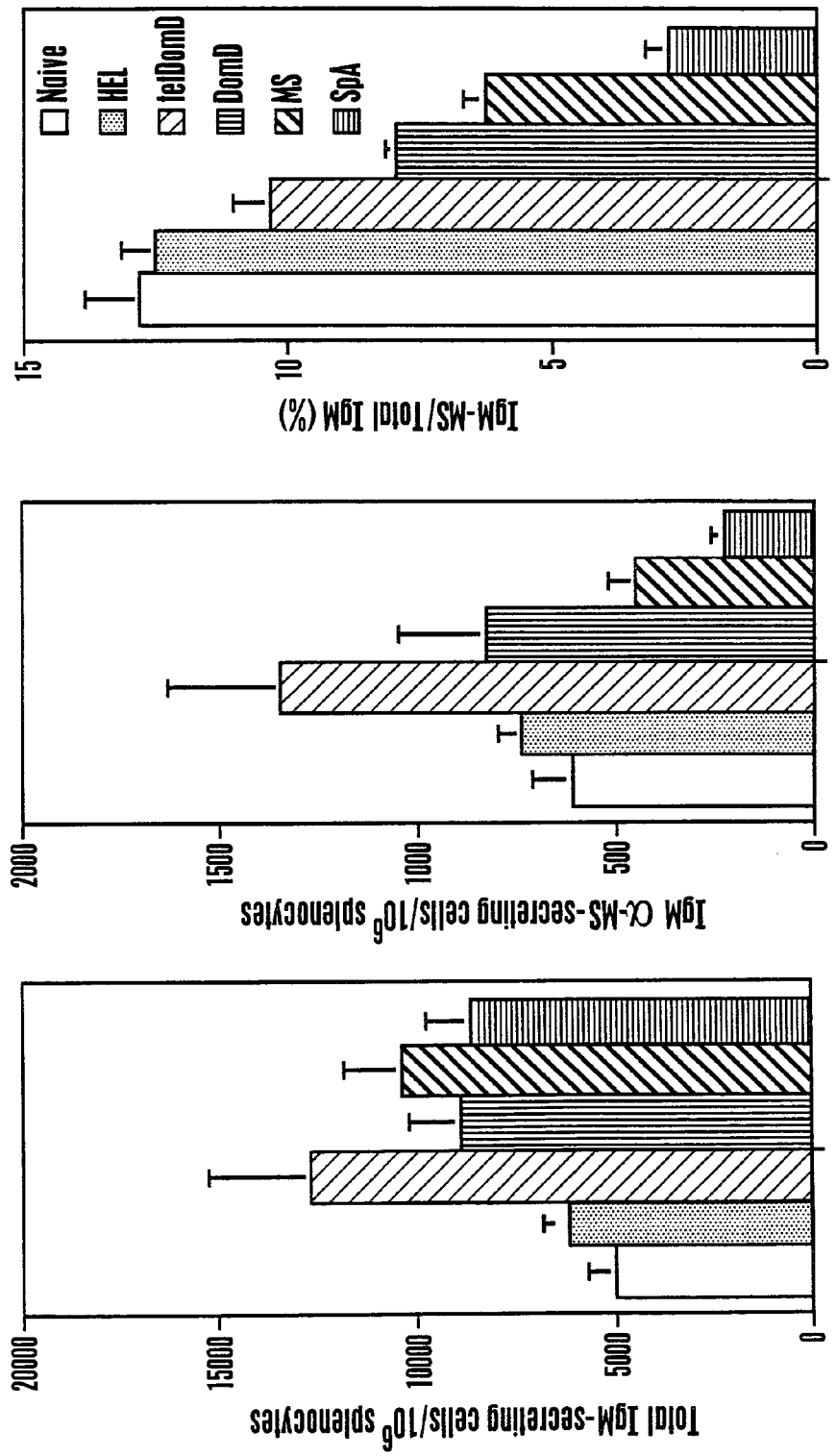

Experiments have been performed on different groups of mice following immune exposure to several genetically or chemically modified forms of SpA which have VHIII Fab-specific affinities/avidities that vary over a >500-fold range (see Table II) to test whether clan VHIII-associated tolerance is greatest in mice treated with forms of SpA with the highest Fab-binding affinity. The impact on the representation of circulating IgM that are capable of non-immune binding interactions with these B-cell SAgs (i.e. clan VHIII) was determined by selective post-exposure effects on SAg-reactive IgM-secreting clones in the spleen and bone marrow in ELISpot assays. Notably, compared to naïve mice, treatment with a protein Ag increased the frequency of total IgM-secreting cells although the specific level varied with each Ag type. Control Ags (OVA, HEL or β-gal) had no effect on the relative proportion of IgM-secreting cells that bound MSPA (FIG. 2). However, the level of suppression of IgM MSPA-specific cells was directly proportional to the relative avidity of Fab-binding activity of the SAg. Compared to naïve and control treated mice, the range of effects varied from near complete loss with the highest affinity form (SpA), to little or no loss with the weakest affinity form (tetmDomD) (FIG. 2). Equivalent correlations were observed for the suppression of circulating MSPA-specific IgM (not shown). These findings illustrate the persistent influence of a B-cell SAg on the composition of the expressed IgM repertoire, and the role of Fab (i.e. BcR)-binding affinity in determining B-cell clonal fate.

Following neonatal treatment With MSPA or SpA, the decrease in the frequency of splenic MSPA-specific spontaneous IgM-secreting cells was found to persist for as long as the treated mice were aged. Even at 70 wks after the last immune exposure, the level of superantigen-specific IgM-secreting cells was still more than 80% reduced compared to naive or control antigen-treated, age-matched control mice. These greatly altered levels of spontaneously MSPA-specific IgM-secreting cells in spleen (68), and in bone marrow (manuscript in preparation), were not affected by the presence or absence of MSPA-specific T cell responses. This suggested that most of the MSPA-binding B cell clones responsible for circulating "natural IgM" had experienced a maturational arrest (i.e. functionally inactivated or anergized) or were clonally deleted. Taken together, these studies document the capacity for this microbial product to induce long-lasting suppression of a component of circulating IgM, which is considered a major component of the "preimmune" defense from infection (discussed further below). It has been demonstrated that using proportionally higher doses of this superantigen (1 mg of SpA or MSPA in saline I.P. every other day for 5 doses), equivalent results can also be induced in adults, and the B-cell repertoire effects last at least 2 months following the last exposure. The same B-cell SAg targeted selective supra-clonal defects could be induced in BALB/c and C57BL/6 mice, and their F1 progeny, indicating that immune response genes do not play an important role in these outcomes. These effects were also seen in TCRβ/δ knockout mice, documenting that T-cell regulation is not required for these induced effects.

The dominance of the VHIII Fab-specific binding site of MSPA in immune responses may be considered as another type of epitope dominance. This phenomena has been associated with structurally simpler Ags (e.g. carbohydrates, haptens or peptides) that induce highly restricted Ab responses. However, in cases of highly restricted responses to protein Ags, the dominant B cell epitopes are generally redundant determinants in functionally multivalent proteins (3;32). While the focused post-immunization B-cell response to SpA (S107 dominated) can be considered as another type of epitope dominance, the high frequency of potential responders and clan VHIII restriction are very different from those of other characterized Ags. Taken together, these properties of a very high binder frequency in the naive repertoire, the immunodominance of the Fab binding site, and the recruitment of a VH restricted responders into the immune response, embody the diagnostic hallmarks of a B-cell SAg. Similar findings would be predicted to occur in response to exposure to a novel SAg with clinically relevant immunologic properties.

Methods:

Methods for quantitation of the frequency of spontaneous Ig-secreting cells have been recently reported (68).

Example 6

B-cell Superantigen Treatment can Greatly Reduce Representation of Certain "Natural" Circulating Antibodies to VHIII-Restricted Conventional Antigen.

As described above, neonatal treatment with a B-cell SAg causes persistent changes in the representation of MSPA-specific IgM, that represent VH family restricted populations affecting >12% of the expressed IgM repertoire (FIG. 2). Based on the above described findings, I postulated that B-cell SAg treatment should also suppress levels of natural (i.e. without specific antigenic challenge) antibodies to certain conventional antigens. To evaluate the impact on the levels of "natural IgM Abs", IgM binding activity was assayed for two conventional Ags that induce VH restricted responses, 4–8 months after the last immune exposure. Therefore, the relative levels of spontaneously arising Abs to phosphorylcholine (PC), which derive from the dominant T15 clone that uses a S107/VclanVHIII-derived H chain was measured. These levels were compared to the antibody level to dextran B1355-S($\alpha$1,3) (Dex), which uses a J558/clan VHI-encoded H chain paired with a lambda L chain.

Figure 3A:
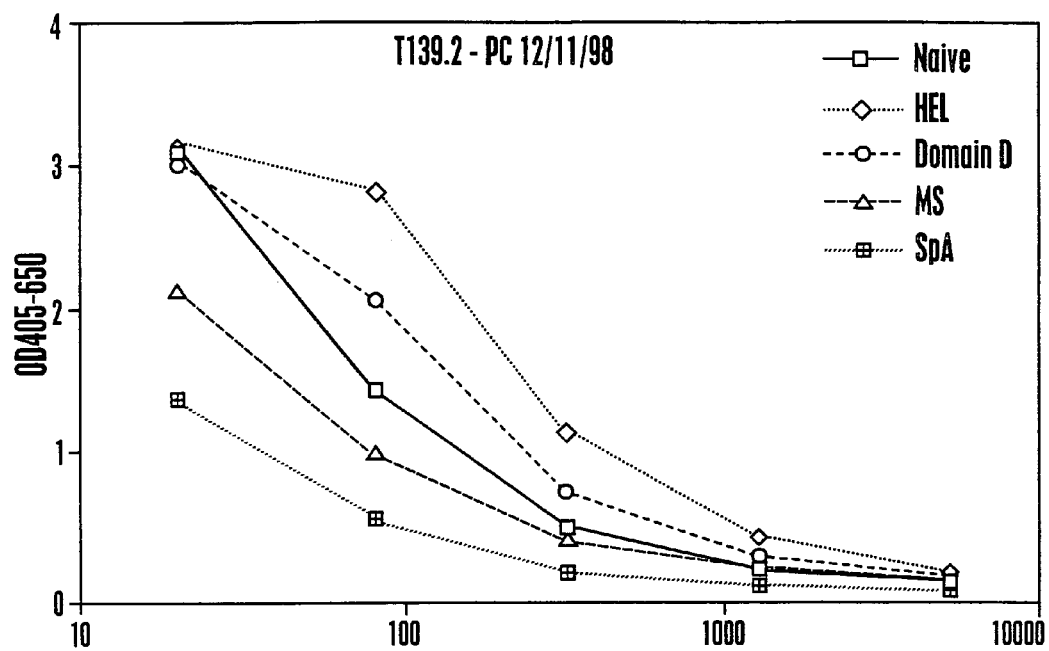
FIG. 3 demonstrates that SpA or MSPA induces persistent loss of natural IgM anti-PC antibodies, which derive from the S107 family. Natural IgM anti α 1.3 dextran antibodies, from the J558 family, are non-specifically increased. Neonatal BALB/c mice were treated with control proteins or different forms of SpA for the first 2 weeks of life, and natural IgM antibody levels were quantitated by ELISA 3–8 months later. SpA, the highest avidity form, induces almost complete loss of natural IgM anti-PC antibodies (S107-T15 set), while MSPA is a somewhat less efficient inhibitor. Treatment with any protein increases the level of total IgM levels, and each has differential but non-specific stimulatory effects on the levels of IgM anti-α 1,3, dextran antibody (J558, clan VHI).
Figure 3B:
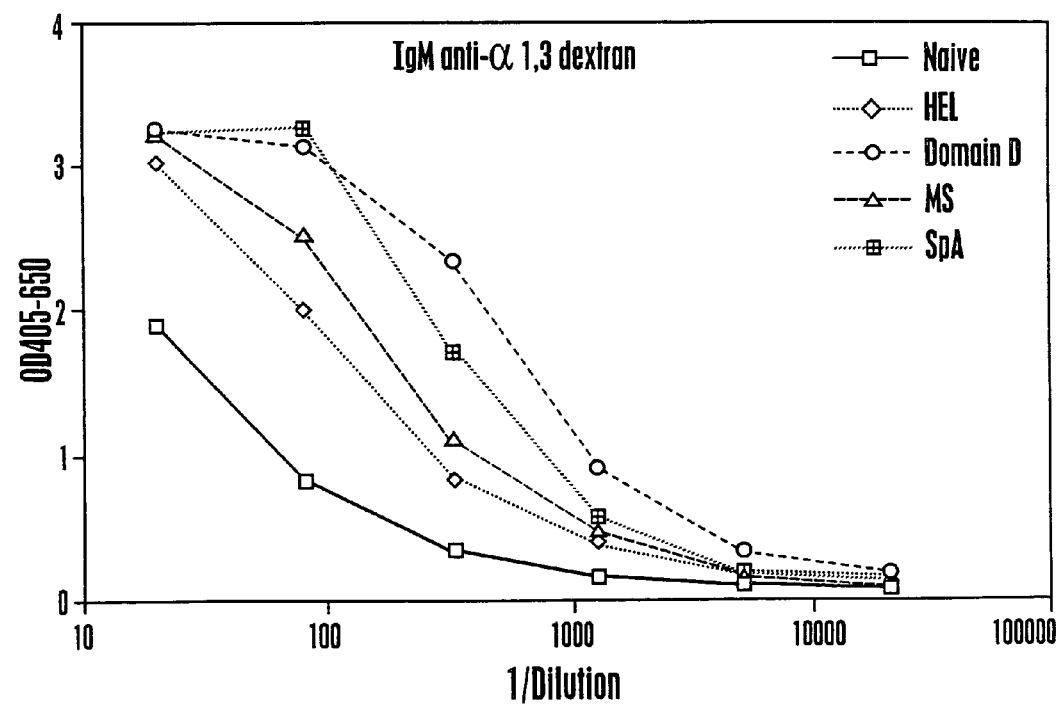

In these ELISA-based assays, wells were coated with Dextran 1355S or PC-BSA, then incubated with dilutions of sera, before development with a lambda or IgM-specific reagent. Parallel to changes in MSPA-specific IgM Abs induced by certain SAg treatments, there were equivalent changes in the levels of IgM anti-PC Abs (not shown). Anti-PC assays with T139.2, a S107/T15-specific anti-idiotype (FIG. 3) were developed to confirm that a clan VHIII Ab set was responsible. Herein, SpA induced the greatest suppression, with lessor inhibition by MSPA, and little or no effects from monomeric domain D. The clan VHIII specificity of inhibitory effect was confirmed in assays of the Ig$\lambda$ anti-$\alpha$ 1,3 dextran Abs, which was most elevated in the SpA-treated mice, with lessor increases in MSPA mice. Similar changes were detected 1 and 2 months after the treatment of 6-mo-old mice with SpA, but not after treatment with the control protein Ag, HEL (Hen egg lysozyme; not shown).

Methods:

As previously described (68), a standard ELISA assay was used to quantify the Ab response to MS and control Ags. Briefly, microtiter wells were coated overnight with protein, dex or c-PS (phosphorylcholine containing) at 5 µg/ml in PBS. After blocking with 2% BSA-PBS, serum samples diluted in block were incubated for 4 hrs at RT. The amount of bound Ab was determined by incubation with horse radish peroxidase (HRP) labeled affinity purified goat F(ab')2 anti-mouse IgM or IgG (Jackson immunoResearch, West Grove Pa.), with values obtained after incubation of substrate for 15 min. The anti-PC response was measured with wells coated with C—PS, and response from the T15 B cell clone (a set of clan VHIII S107-encoded antibodies) was determined by development with a saturating concentration of the T15-specific rat IgG1, T139.2 (13)(kind gift of Dr. Matthew Scharff, Albert Einstein College of Medicine, N.Y.). The clan VHI J558-encoded antibody response to $\alpha$1,3 dextran was determined by development with HRP-labeled anti-$\lambda$ reagent (Jackson Labs). For quantitation, total IgM, IgM anti-MS responses, IgM anti-C—PS, and T15-encoded anti-C—PS all used standard calibration dilutions of a monoclonal T15-IgM antibody, EO6. For the anti-dextran responses, M104E was used (54). To compare Ab levels, values from different groups of mice were compared at sample dilutions at which the lower mean signal provided an OD of ~1.

Example 7

Relative Suppression of MSPA-Binding IgM Correlates with Loss of clanVHIII Gene Family Expression

Figure 4:
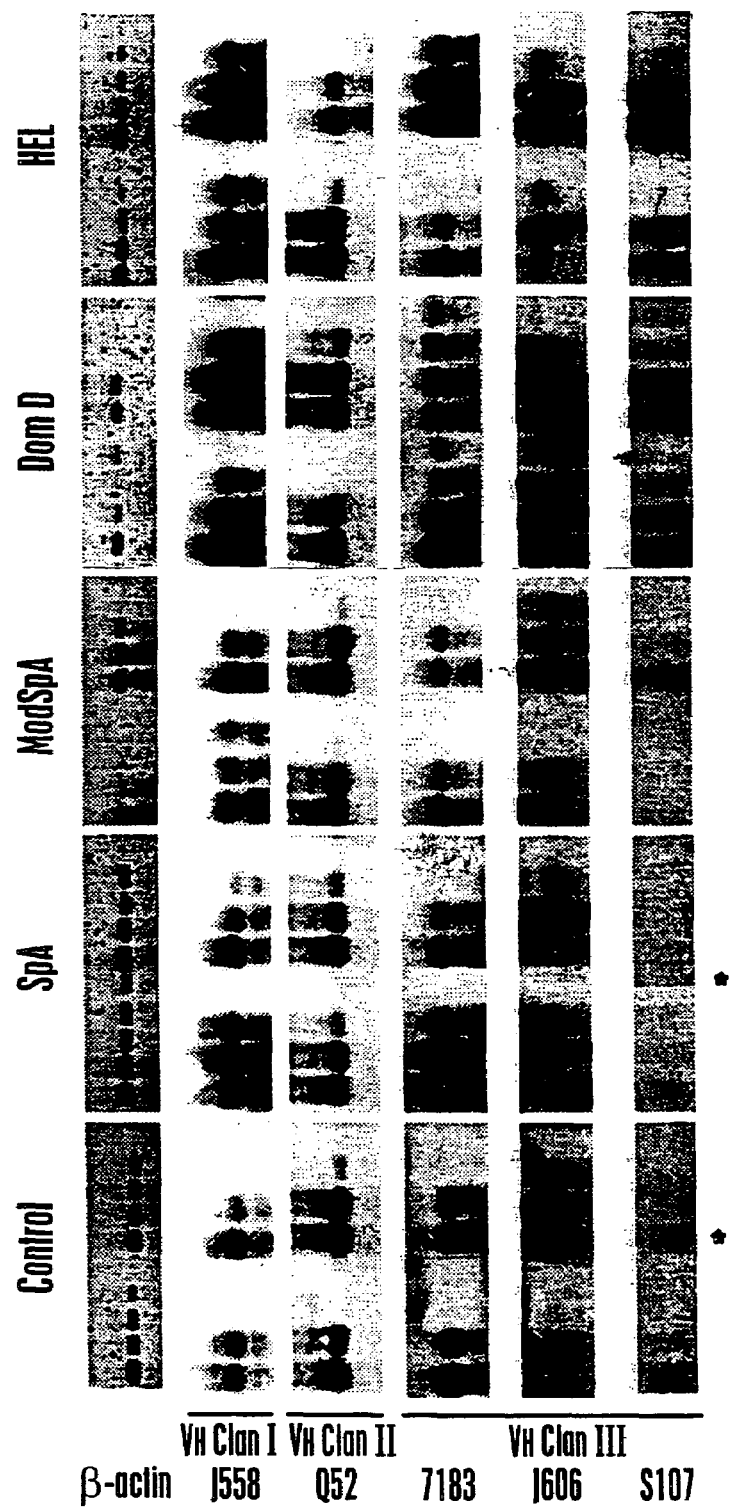
FIG. 4 shows that SpA or MSPA induces persistent loss of splenic S107-mu mRNA expression. Neonatal BALB/c mice were treated with different forms of SpA for the first 2 weeks of life, and VH family-mu expression was quantitated 3–8 months later. Using seven different VH FR1-specific primers, family-mu expression was quantitated 3–8 months later. Using seven different VH FR1-specific primers, expression was measured by RT-PCR-Southern blotting for clan VHI (J558, Vgam3), clan VHII (Q52), and clan VHIII (S107, J606, 7183).). For each reaction type, five 5-fold serial dilutions of the cDNA were amplified. In addition to the β-actin product, products of seven VH families were examined, with results for three families presented. The results from two mice, representative of the groups of four mice, are presented. Compared to HEL-treated mice, which was associated with expression of all VH families, there was a selective loss of only the VH clan III/S107 family with SpA treatment, with a lessor effect with MSPA treatment. Treatment with any protein increases the level of mu transcript expression, although control protein antigens (e.g. HEL, OVA or p-gal) do not alter the relative representation of the different VH families. SpA, the highest avidity form, induces almost complete loss of S107-mu transcript expression, while MSPA is a somewhat less efficient inhibitor. The monomer of SpA, domain D', does not alter relative VH family expression. Similar effects were documented after treatment of adult mice (not shown).

To evaluate whether neonatal treatment with a B-cell SAg selectively affects B-cell that express certain clanVHIII genes, semi-quantitative RT-PCR/Southern analysis for the relative expression of mu-rearrangements from seven major murine VH families that represent >85% of the expressed splenic repertoire in naïve adult BALB/c mice were performed. In these studies, compared to HEL-treated mice there were no significance differences in MSPA or SpA-treated for the expression of clanVHI (i.e. J558 or Vgam3) or clanVHII (i.e. Q52) family expression. While amplifications with primers designed for three other clanVHIII families were also evaluated (i.e. 7183, J606 and X24), the only significant decreases were demonstrated for S107-mu rearrangements. Significantly, in each group of four age-matched mice, the decrease im S107-mu transcript expression was greatest in the SpA-treated mice. These studies provided unbiased surveys of VH family usage documenting dramatically decreased S107 family expression in MSPA and SpA-treated mice. This effect was documented whether these SAgs were administered during the neonatal period or adult phase of life. These studies further document that the magnitude of the biologic effects is directly linked to their relative affinity/avidity of the B-cell SAg (see FIG. 4). Clearly, these same methods can be used to look for the immunologic imprint of B-cell SAgs of any VH specificity. Using a parallel set of VL family-specific assays, the same approach could be used to survey for a response to a VL-specific B-cell SAg.

To obtain a more quantitative determination of the loss of S107 expression, the oligonucleotide primer sequences used for amplification of the S107 family-mu rearrangements were adapted for use in a quantitative assay using the TAQMAN™ apparatus (Applied Biosystems). These studies employed a S107-family specific FR1-sequence derived fluorochrome tagged oligonucleotide to quantitate family specific products. These studies demonstrated prolonged suppression of expression of the S107 family, with a mean value of greater than 92% reductions in MSPA or SpA-treated mice, compared to HEL-treated mice for 1–4 months after the last adult or neonatal treatment, in groups of at least 4 age-matched mice. In these studies, RNA content was independently normalized by measurements of the content of the GADPH "housekeeping gene."

Methods:

RT-PCR-Southern assays. Total RNA from control and MS treated mice was isolated from $40 \times 10^6$ fresh splenic cells, and 3 µg of total RNA reverse transcribed in a 20 µl volume using a previously reported protocol (68). For the amplification of murine genes, $\frac{1}{10}^{th}$ of the first strand reaction product was added to a mixture containing 5 µl of 10× PCR buffer (Boehringer-Mannheim, Indianapolis, Ind.), 5 µl of 25 mM MgCl$_2$, 1 µl of 10 µM dNTP (Pharmacia), and 1 µl of each 50 µM primer solution (Operon, Alameda, Calif.). Nuclease-free H$_2$O was added to a final reaction volume of 49.5 µL. Amplification conditions included a hot start of 95° C. for 3 min, with the addition of 2 U of Taq Polymerase (Boehringer-Mannheim), then 30 cycles of 95° C. for 1 min, 60° C. for 1 min, and then 72° C. for 1 min, followed by a final 72° C. for 5 min, in a Perkin Elmer 9600 thermal cycler. The content of β-actin cDNA using previously described methods (40;68). Each of the $V_H$ family-specific separate reactions employed the same antisense mu $C_{H1}$-derived oligonucleotide primer (5' ccc atg gcc acc aga ttc tta-3') and a different sense FR1 derived oligonucleotide, as previously described (68). Specificity was confirmed by sequencing and hybridization studies (9; 18; 19). Products were individually stored at −20° C. Aliquots from each PCR sample were separated on a 2.5% agarose gel, and stained with Sybr Green Dye II™ (Molecular Probes Inc., Eugene Oreg.). Gel images were directly digitized using a Storm PhosphorImager™ (Molecular Dynamics, Sunnyvale Calif.), as per the manufacturer's protocol. PCR products were transferred to N+ nylon membrane (Amersham Pharmacia Biotech, Piscataway N.J.), and probed with VH family-specific prepared plasmid probes (gift of Roy Riblet, Medical Biology Institute) labeled to a specific activity of $10^6$ cpm/ug, using $2.5 \times 10^6$ total counts per 2 ml of hybridization solution, with previously described methods (9). Hybridization signals were collected using the PhosphorImager™, and analyzed with ImageQuant™ (Molecular Dynamics) using linear regression Example 8

SAg treatment Inhibits the Immune Response to a PC-Directed Anti-Pneumococcal Vaccine.

The above described studies evaluated the composition of the "natural" IgM repertoire, which represent the Ig products that are spontaneously secreted into the circulation without specific antigenic challenge. In fact, substantial levels of T15-derived IgM anti-PC antibodies are also present in the circulation of outbred mice, and mice raised in germ-free and "antigen-free" environments, suggesting that gut flora or antigenic exposure in the gut does not select this part of the expressed "natural" repertoire. In fact, both T15 anti-PC and the α1,3 dextran-specific response has been reported to be linked to the B-1 pool of extra-follicular B cells.

The effect of SAg treatment on the response to challenge with a conventional Ags was evaluated to determine if the broad effects of SAg treatment on the "pre-immune" repertoire, might also affect the B-cell precursor frequency in the responses to certain conventional antigens. To this end, the response to a Thymus Independent-2 (TI-2) form of a vaccine to PC, which has been previously widely used for the induction of a PC-specific responses, was assessed (10). For these studies, a heat-killed form of the R36A pneumococci, and administered doses equivalent to $10^8$ killed bacteria emulsified in complete Freund's adjuvant (CFA) either I.P. or subcutaneously was used. To each dose was added an immunogenic dose of α1,3 dextran, to determine if an antigen-specific tolerant state was induced in a challenged animal. Mice were prebled, immunized, and then plasma collected 10 days later for analysis. Antibody responses were assayed as described above, and values determined in relative units (RU) by comparison to known dilutions of an appropriate Ag-specific IgM Moab incubated at several dilutions on the same plate.

Figure 5A:
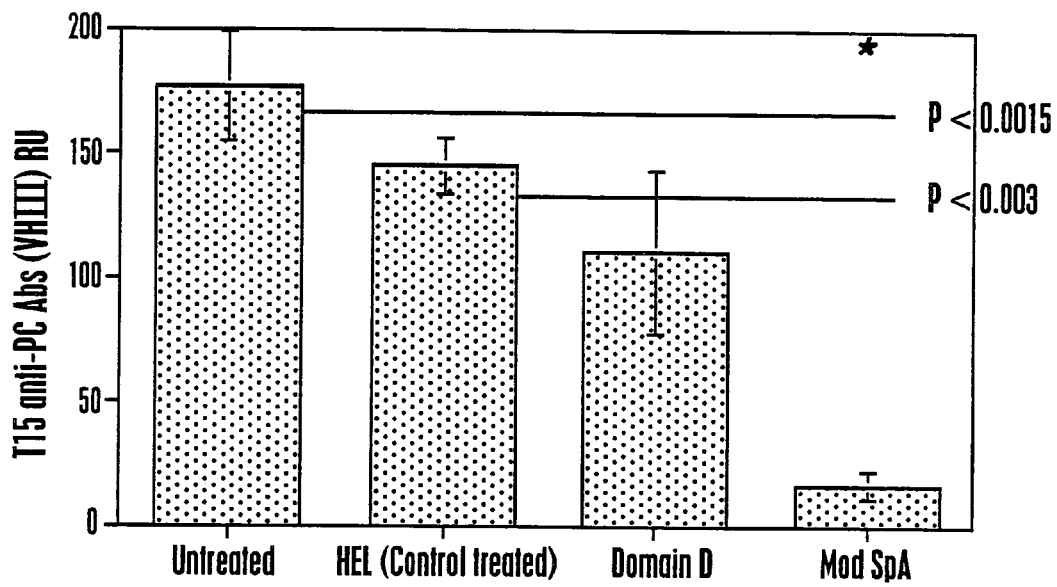
FIG. 5 shows that neonatal treatment with SpA causes a persistent tolerance in adult mice to challenge with a PC-specific vaccine. In these studies, results were compared to age-matched Naïve mice. Groups of 3–4 mice were challenged at 3 months of age by intravenous injection with immunogenic doses (2 µg in saline) of killed R36A pneumococcal bacteria and dextran in CFA). T15 and anti-PC responses and anti-dextran were evaluated by ELISA 10 days after challenge. Significant responses (mean±SEM) were responses to PC in every challenged mouse that did not receive neonatal SAg treatment (Naïve/C-PS). However, significant anti-PC responses could not be detected in any mouse that had received neonatal treatment with SpA. α 1,3 Dextran induced a specific antibody response in each immunized mouse. These studies provide the first documentation that a B cell SAg can induce tolerance to a conventional Ag.
Figure 5B:
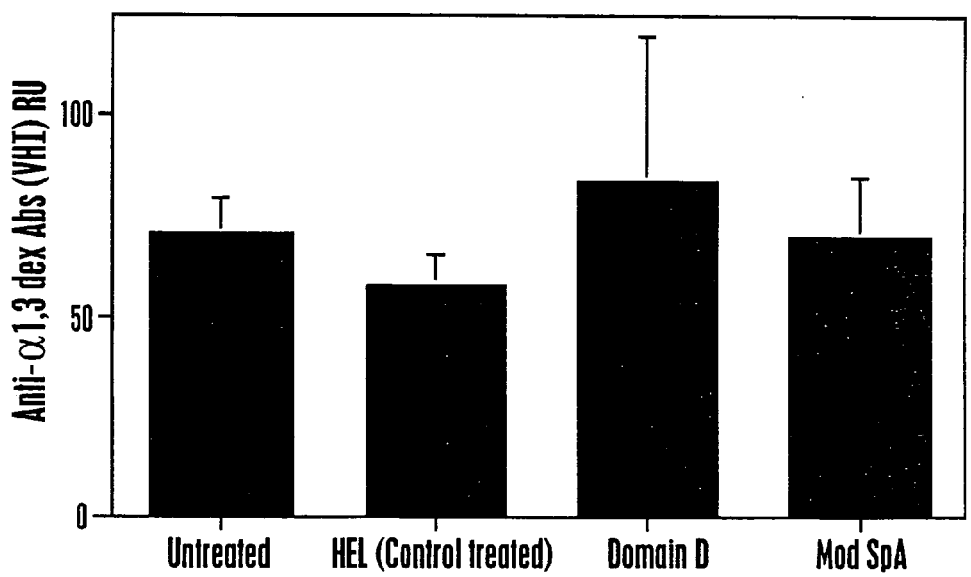

In FIG. 5 are displayed results from a representative study. Neonatal treatment with MSPA or SpA (not shown) were shown to induce tolerance in T15 anti-PC responses, while mice treated with control protein antigens had vigorous responses. While the SpA and MSPA treated animals developed T15 anti-PC antibody levels higher than pretreatment levels, comparisons indicating that they were not greater than in mice that received CFA alone. In contrast, the clan VHI-restricted anti-α1,3 dextran response was robust in every animal challenged. These studies suggest that a B-cell SAg can selectively alter the functional competence within the B-cell compartment.

The above results in neonates were confirmed in Ig transgenic murine systems. In both normal and trangenic systems, SAg or MSPA-treatment results in a persistent SAg-specific clonal deficit within the B-1 compartment, suggesting that the observed tolerizing effects are due to clonal deletional mechanisms. In adult mice, it has been reported that these B-1 cells are not be replenished from the adult bone marrow, while B-2 cells may be continually replenished. However, these clonal deletion effects are not limited to B1 and B2 cells. Any B cell can be deleted or tolerized provided it expresses a VH region reactive with the superantigen. With regard to pathogenic B-cell clones, their selective deletion, particularly at anatomic sites of autoimmune destruction, would probably be beneficial even if related lymphocyte populations later slowly returned over time.

Example 9

Introduction to Phage-Display Technology Approaches for the Isolation of Desirable SpA Domain Variants Phage-display technology originated with the observations of George Smith, who demonstrated that oligonucleotide-based DNA sequences could be introduced into the 5' end of the gene III, minor coat protein gene, facilitating expression of the surface of a filamentous bacteriophage (76). By this approach, libraries of proteins can be arrayed on an assembled phage that contains a copy of the vector with encoding gene. Different vector designs enable monovalent, oligovalent or even polyvalent surface displays of up to 100's of copies per phage. Moreover, libraries containing $>10^8$ individual members can be readily generated, and following library amplification the resulting phage preparations contain $>10^{11}$ colony forming units (cfu) per ml. There are many advantages over conventional library methods (e.g. λgt11 vector), for which laborious genotyping or phenotypic screening methods may enable evaluation of at most ~100,000 clones. Using solution-phase phage libraries, clones with desirable function properties can be directly and efficiently isolated and amplified based solely on binding interactions of the phage-surface displayed recombinant fusion protein. A variety of selection strategies are available, including selection on ligand immobilized on a solid phase microtiter well or affinity matrix. Alternatively, selection can be performed on the surfaces of viable cells (62). In many reports, a single round of selection can result in >100-fold enrichment for clones with desirable binding properties. Each complete round of amplification and selection is performed in a 24-hr cycle. Moreover, initial rounds of selection are generally associated with enrichment for binders, while in later rounds competition between binders yields selection based on highest relative affinity (i.e. slowest off-rates).

The highly stable secondary structure and high bacterial expression levels of SpA derivatives have contributed to the compatibility of these genes with phage-display technology approaches. Most studies have used the well characterized domain B, but as described herein, a fully functional monomer of domain D can be displayed fused to the N-terminus of the gIII coat protein (described above), that enables efficient selection from dilute libraries based on IgG binding activity (14;38).

Phage-display libraries based on SpA domains have provided remarkable successes for the engineering of small functional domains with novel or optimized binding activities. Notably, by exploiting the detailed understanding of structure of the IgG Fc-SpA complex, Wells and colleagues designed a strategy to create even smaller protein derivatives with the same functional capacity of SpA. By creation of libraries of domain Z, based on the helix I and II of a SpA domain but including certain codons with randomized sequences. By this approach, a 34-residue analogue, termed Z34C, was isolated that exhibits a novel inter-helical disulfide bond that enhanced stability, and a 9-fold enhanced IgG binding activity. Moreover, Z34C folds into a structure virtually identical to the equivalent region in native SpA domains. Thus, this stabilized two-helix peptide, about half the size and with one-third of the remaining residues altered, accurately mimics both the structure and function of the native domain (8;77). This engineered protein analogue represents one of the smallest functional peptides with features typical of a folded protein.

In studies that provided the proof-of-principles for these strategies, libraries were created in which the gene for SpA domain Z was used as a scaffold, from which stable domains with novel binding activities were selected. Guided by NMR and crystallographic reports, residues involved in stabilizing the hydrophobic core were conserved, while the codons for 13 non-contiguous surface-exposed residues of helix I and helix II were randomized, including seven residues involved in Fc binding. By this approach, non-complete libraries of less than $10^8$ members were created (47;48) and "affibodies" of diverse specificity were subsequently recovered after 3–5 rounds of selection, including binders to Taq DNA polymerase, human insulin and human apolipoprotein. Notably, recombinant clones exhibited conservation of the parental alpha helical structure, and their novel binding activities were highly specific with μM dissociation constants, KD. These studies demonstrate the use of the stable secondary structure scaffolding of SpA domain to build novel binding activities.

Example 10

Isolation of SpA Variants with Improved Clan VHIII Binding to Abs and B Cells.

Rationale: To isolate variants of a SpA domain with enhanced VHIII Fab-binding activity, large libraries based on domain D of SpA will be created, in which codons for residues composing the VH binding surface have been randomized to encode for all possible amino acids. From these libraries, several strategies to select for variants with greatly enhanced VHIII-specific binding activity can be pursued.

Background: The VH region binding affinity of a SAg directly correlates with its immunosuppressive/tolerizing/ deleting properties. The residues in helix II and helix III of domain D of SpA that naturally conform to the VHIII-Fab binding surface have been identified (see Table I). Following oligonucleotide-based randomization of codons for these surface-exposed residues and other surface exposed residues related to the Fab binding site, domains with enhanced binding Ig-binding activities will be isolated.

In specific, the localization of the SpA contact sites for clan VHIII-encoded Ig adds greatly to the economy of methods required to attain the composition and the methods described herein. Phage display technologies clearly offer the most efficient means for the recovery of mutant SpA domains with altered and optimized binding properties. In fact, it is difficult to imagine a strategy currently suited to these goals.

These structural studies simplify the strategy and make success in these investigations a near certainty. Admittedly, there are limits to the size of a phage-display library that can be currently practically generated and screened. Using methods currently in practice, one can readily generate libraries of $\sim 10^8$–$10^9$ independent members, and if necessary one can use packaging methods using λ bacteriophage arms (2) that improve transfection efficiencies enabling generation of libraries with $10^{10}$–$10^{11}$ independent members. To attain these goals, complete libraries that include all possible codon sequence randomizations for only 6 codons or less are created. Given the 20 possible amino acids (which may not be necessary), a library with a minimum of 206 members (i.e. $6.4 \times 10^7$) is required. Therefore, the ability to create libraries of SpA domains of the desired size is currently feasible.

In a primary strategy, libraries will be selected against monoclonal Abs directly immobilized onto microtiter wells, or biotinylated monoclonal Abs captured onto streptavidin-coated wells. These selection methods, and subsequent analyses to characterize Ig binding specificity, will be facilitated by making a large panel of purified human and murine monoclonal antibodies with diverse V region sequences of known sequence. Alternatively, selection will be directed against cell surface-associated monoclonal Ig on B-cell hybridoma cells (gift of Tony Marion, University of Tennessee). Binding specificity will be assessed by ELISA and BIAcore studies. B-cell SAg binding studies by flow cytometric assays will be performed on polyclonal lymphocyte populations, and mononuclear B cells that express BCR encoded by defined V genes.

Example 11

Creation of Variants of SpA with Altered Specificity for Distinct $V_H$Clans.

As reported (57;71), the DNA sequences of variant SpA domains will be determined using an automated sequencer (Applied Biosystems), with analysis using MacVector 6.5 software (Oxford Molecular), and the deduced protein sequence determined. Correlations with the 3-D model of the SpA-2A2Fab complex as described herein provides the structural basis for documented functional improvements in an SpA variant.

Rationale: To create variants of SpA domains with greatly altered unconventional specificities for different VH family/clan-defined sets of BCR. These studies will exploit the libraries created from the above described approach, and the known overall conservation of the Ig fold in the products of diverse VH families. Variant domains are selected that are specific for the products of the clanVHI, or the clanVHII, to complete a panel useful in B-cell repertoire surveys (i.e. supra-clonotypic markers). These reagents should also enable the subsequent development of new experimental systems involving SAg targeting of pathogenic autoreactive or neoplasitic B-cell clones (e.g. anti-red cell (44)). Following recovery of these novel domain variants, engineered forms with multiple domains will be created, and the biologic activity evaluated in section 3.

Background: In murine and human Abs, the overall Ig β-strands are highly superimposable. The greatest variations between different Abs is in the β bends (i.e. CDR loops), that form the conventional Ag binding sites. However, β-loops are not involved in the Fab-mediated binding of SpA. Hence, between different VH clans, the VH surface targeted by a B-cell SAg varies predominantly based on the amino acid side chains of a very limited number of VH clan-specific residues in FR1 and FR3 that are surface exposed. Therefore, using the libraries described above, SpA variants specific for these distinct VH clan sets should also be selectable.

Selection of clan $V_g1$-SAgs. In the mouse, B-cell expressing clan VHI (i.e. mostly J558 and Vgam3) genes represent more than half of the repertoire. There are also several well developed transgenic VHclanI transgeneic murine B cell tolerance systems, that would be attractive for investigation of SAg studies, if appropriate clanVHI specific SAgs were available. In addition, the α1,3 dextran (B1355-S) response is encoded by a J558 V gene. Like the anti-PC response, the anti-α1,3 dextran response is a TI-2 response linked to the B1 pool. Hence, this system is an attractive means to test whether findings in VHIII-limited SpA-induced responses illustrates common features of B-cell SAg interations with the immune system. These studies will follow the same strategies outlined above. Initial rounds of selection will be against MOPC104E, the prototypic J558-encoded, α-1,3 dextran-specific Moab. Later rounds may be selected by a human VH1 Ab, such as Bor, which is a prototype clan VHI Ig that is a cryoglobulin-associated monoclonal RF (67).

It should be appreciated that for each of these efforts, it may only be a first step if one recovers a SpA variant of the desired VH specificity but with inadequate affinity. From this beginning, one can create a degenerate SpA gene "daughter" library, in which the selected codon sequence variation is fixed but randomize additional SpA codons that are predicted to interact with other VH residues. By these sequential steps, one should be able to increase the intrinsic affinity of the novel VH-specific binding interaction, by reiterating an approach that has been successfully applied in antibody engineering exercises (4).

Selection of clanVHII-SAgs. Ideally, to complete the panel of SAgs capable of surveying the expression of all VH gene families, domains specific for the clanVHII will be generated. These reagents may have special utility for the treatment of chronic cold agglutinin syndrome in humans (especially the most common I and i red cell specificities). This disease is caused by a monoclonal Ab encoded by the expression of a single clanVHII gene, human V4–34, in diverse rearrangements, and paired with diverse L chains (64;67). Hence, treatment with a SAg agent with the appropriate VH4-specificity could selectively remove this clone, while not affecting the remainder of the B cell compartment. In addition, a clanVHII-specific reagent might also be useful for the treatment of SLE, which has been reported to be dominated by over-expression of the VH4 family (12). For these studies, the strategies outlined above will be pursued, using a large panel of human VH4 family-encoded Abs for selection (75).

Figure 1B:
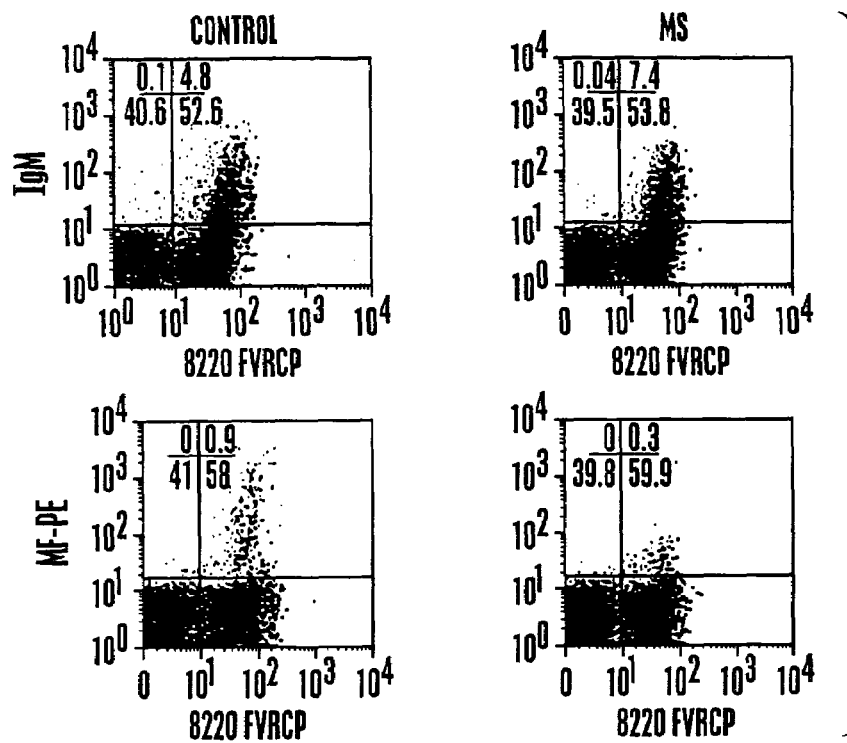
Figure 1C:
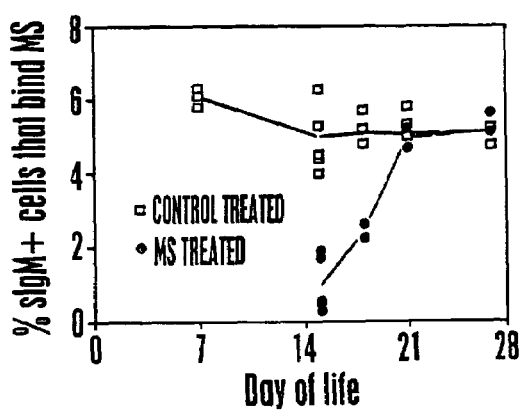
Figure 6:
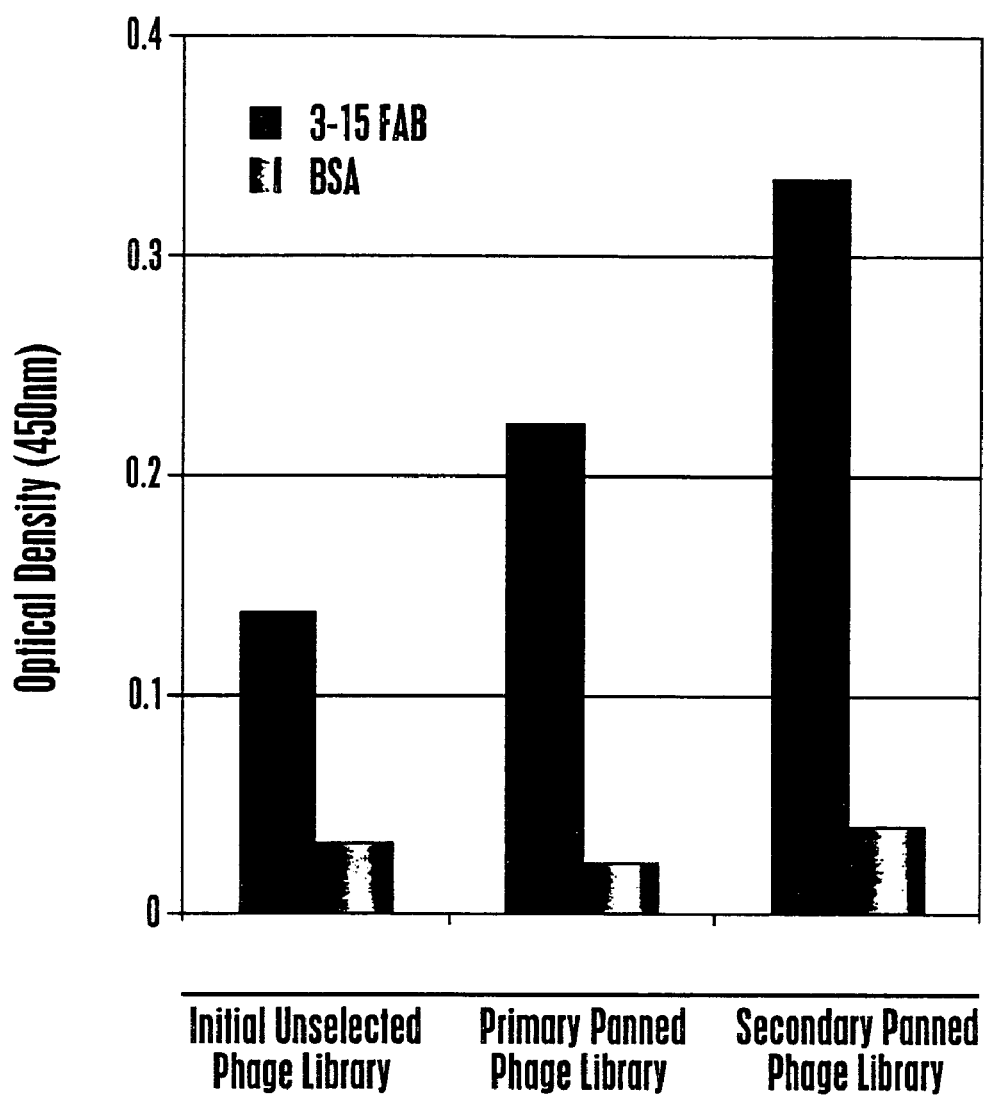
FIG. 6 is a molecular graphic showing domain D overlay on $V_H3$ Fab (2A2, upper left panel) and of the $V_H4$/clan II Fab (7FAB, upper rt panel; 1BVL, lower left panel; and 1JRH, lower right panel) antibodies. Overlay on $V_H3$ Fab of 2A2 is based on crystallographic analysis of the 2A2 Fab complex with domain D. Highly charged areas are depicted as shaded areas. The peptide backbone of domain D is depicted along with associated side chains that were shown to contact Fab 2A2. Other panels are based on structural modeling data aligning the overall secondary structures of the $V_H4$ Ig shown in likely association with the domain D peptide backbone. Cationic surfaces are blue and anionic are red.

FIG. 1 shows a molecular modeling alignment of several VH4/clan II Fab domains with SpA domain D. It is noted that Vh4/Clan II Fab do not share topographic features that would completely disallow a variant domain of SpA to juxtapose its surface to that of a VH4/clan II antibody. After establishing that the VH4 Fab binding face was accessible for a domain D variant, it is considered that the amino acid side chains would interact with the hydrophobic/hydrophilic side chains on the Ig Fab face. FIG. 6 demonstrates that $V_H4$/clan II Fab share features of their surfaces that are distinct from the analogous surface of a $V_H3$ Fab, like 2A2. Notably, $V_H3$ antibodies have a hydrophilic, cationic pocket that enables the electrostatic interaction with the side chain of Asp36 in domain D, and this pocket is absent from VH4/clan II Fab. By overlaying the backbone of domain D and adding the side chains of that project toward the VH region surface, the positions in the SpA domain D that might disallow the close apposition of the surfaces of these two molecules were studied. These types of analyses indicate that $V_H4$ Ig have a clearly different binding face both structurally and electrostatically. It was also established that there are no inherent features that would disallow the formation of a structurally relationship between a $V_H4$ Fab and an appropriate variant domain of SpA that retains the triple alpha helical bundle structure.

Example 12

Creation of Phage-Display Libraries Displaying Variant SpA

An approach to isolation of variant SpA domains with novel binding activities uses the display of functional SpA variants on the surfaces of filamentous phage.

Demonstration of SpA Phage Display

The feasibility of this goal has been shown by displaying a functional SpA D domain on phage using the vector, pCOMB3H.

A source of the SpA domain D that includes the specific mutations Leu17Asp and Ile31Ala was cloned into the pRSET vector as previously reported (Roben et al.,. *J. Immunol.* 154:6437–6446 (1995)). The oligonucleotide primers, pC3H S and pC3H AS, (see Table V) were used to amplify the gene encoding this SpA domain D. Subsequent cloning of the resulting amplimer product was aided by the incorporation of compatible Sfi I restriction sites into the oligonucleotide primers. Using these sites, the domain gene was directionally cloned into a compatible in-frame site in the pComb3H vector. The result of this cloning is that the gene for the SpA domain is in-frame with the upstream bacterial leader sequence and also in-frame with the downstream truncated gene for the filamentous phage coat protein, gpIII.

Using standard methods, an aliquot of a suitable strain of *E. coli* was then transformed with this plasmid, pCOMB3H-domain D mutant gene. The transformed bacteria were rescued with helper phage, enabling the display of the cloned gene on the surface of the phage. In practice, there are often variant plasmids created by this process, and many of the resultant clones are defective for the display of the desired gene due to amplification or cloning artifacts or other mechanisms. A limited number of rounds of library panning against a $V_H3$ IgM Fab, termed 3–15, which was immobilized on an ELISA well, was performed.

Figure 7:
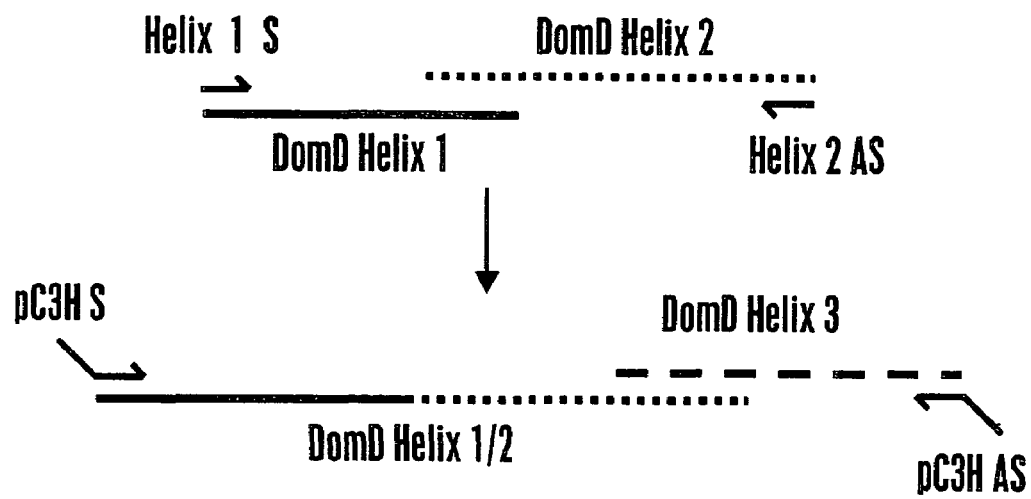
FIG. 7 shows the binding to Fab of a mutated domain D library expressed on M13 phage. Equal titers of each phage were added to wells coated with a $V_H3$ Fab, 3–15 Fab, or a central antigen bovine serum albumin (BSA). Compared to the original unselected library expressing the mutant domain D construct, with each sequential round of planning, there was specific enrichment for 3.15 binding activity.

Following panning, the resulting selected libraries following were evaluated in a standard phage binding ELISA (FIG. 7). Here, binding of each of the sequential libraries to wells coated with the $V_H3$-encoded antibody, 3–15, was compared. Wells coated with bovine serum albumin (BSA) were also included as a negative control to ensure that binding was specific for the immobilized protein. Equivalent titers of phage from each library were added to these wells.

The results from the phage ELISA showed specific binding activity of these phage to 3–15 (FIG. 7). DNA sequence determinations of the plasmid isolated from three individual bacterial colonies from the selected library verified that they contained the in-frame gene for the domain D Leu17Asp and Ile31Ala mutant gene. These data document that a functionally active mutated SpA domain can be successfully displayed on filamentous phage, and specific clones can be selected by virtue of Fab binding properties.

Creation of a Library of Variant SpA with Impaired Fc Activity

Libraries based on a scaffold encoded by the DNA sequence of Leu17Asp/Ile31A mutant domain D, which has greatly impaired Fc binding activity also can be created. These libraries will be constructed from three synthetic oligonucleotides. To facilitate cloning into the pCOMB3H phagemid vector for monovalent gene III display (55), introduction of SfI (8-cutter) restriction sites for directional cloning of the designed sequence will be used. The first oligonucleotide will be invariant and will include the upstream SfI site and most of the sequence for helix I that is not involved in Fab binding, representing about 80 nucleotides of the 61-codon SpA domain. The second oligonucleotide will be the most degenerate. It will include randomized codons for the helix II contact residues of Gln26, Gly29, Gln32, Ser33 and Asp36, using the NNK nucleotide doping strategy, in which N is any nucleotide while K is either G or T, which allows for all 20 amino acid combinations within 32 codons. The third oligonucleotide will encode for the helix III with randomized sequences only for the Glu47 codon, followed by a downstream SfI site.

As presented in Table III, randomization of these residues will affect every contact site for which products of clanVHI offers a different VH residue. Hence, within the design of this degenerate SpA domain library one should be able to select clanVHI specific SAg. Design of these oligos will include repeated flanking sequences to enable efficient overlap PCR to "sew" together these DNA pieces into the total gene sequence. Special efforts, including HPLC purification of oligos, and PAGE purification of the final overlap products, will be performed to remove truncated DNA. Adapting standard methods well documented in recent publications (55;57;71), the library will be ligated into prepared pCOMB3H vector, then electroporated into competent XL1-blue bacteria. If necessary, sequential transformations will be performed until a library of the desired size is attained, or lambda packaging will be used. Afterward, the library will be amplified and rescued in the phage-display form that enables panning for selection of variants with optimal binding activity.

To create a SAg specific for the products of the clanVHII, selection can proceed with the above described library, and then binders evaluated using in vitro assays. If these selected clones demonstrate consensus sequences in codons that had been randomized, this is evidence of in vitro selection. These clones will be used in subsequent studies, if affinity measurements provide KD ~$10^6$ M for the binding of products of diverse members of a VH family. If affinities are unlikely to induce desirable in vivo responses, daughter libraries can be made in which the selected codons are maintained and additional codons for the Asn43, Val 44, Glu 47 in the SpA domain, are randomized, as per the strategy outlined above. The same approach can then be used to evaluate for successful selection of useful SAg variant domains. A similar approach can also be used to try to enhance affinity in clanVHI-specific Sap variant domains.

Preparation of an SpA Variant Library:

A example of how to alter chosen amino acid residues at or near the Fab binding site in SpA that generates the degenerate library from synthetic oligonucleotides that include certain positions that are degenerate or variegated for the incorporated nucleotides is provided. While most of the synthetic oligonucleotide corresponds to the DNA sequence of the native domain D gene sequence, certain nucleotide positions were variegated at positions correlating to the codons for amino acids identified for randomization based on structural analysis and modeling of SpA-Fab interactions. For technical reasons, it is best to limit the size of a synthetic oligonucleotide, and therefore three different long oligonucleotides were synthesized that each include certain complementary sequence intervals enabling overlapping for subsequent amplification of longer double stranded DNA fragments. By this approach the entire length of the synthetic degenerate domain gene library can be built from smaller pieces of synthetic DNA.

To generate degeneracy at designated codons, one can use the degenerate codon sequence NNK to randomize certain specific codons (N=A, G, T or C; and K=G or T). NNK therefore encodes for 32 codons that cover all 20 natural amino acids, but also including the TAG (amber) termination signal. The theoretical combinatorial library size, if full and simultaneous NNK degeneracy is achieved at all of the seven selected positions that have been identified for this initial library, would be ~$1.3 \times 10^9$ protein variants or $3.4 \times 10^{10}$ different DNA sequences. However, using the standard bacterial transformation methods of electroporation, it is estimated that the potential library size routinely achievable is $1 \times 10^7$ to $1 \times 10^{10}$. Hence, for this library it is possible to have incomplete representation of all possible variations.

However, this may not be a problem based findings from previous reported work on similar libraries in which residues relevant to the Fc binding site of a domain of SpA were randomized (Nord et al., *Nat. Biotechnol.* 15:772–777 (1977); Nord et al., *Protein. Eng.* 8:601–608 (1995)). In these studies, based on the synthetic domain Z of SpA (which is devoid of Fab binding activity), a library with an estimated size of $4 \times 10^7$ members was generated that included 13 randomized codons. However, if 13 codons were completely randomized by this NNK strategy it would have required a library of ~$8.0 \times 10^{16}$ protein variants from $3.7 \times 10^{19}$ DNA sequences to include at least 1 copy of all possible variant molecules. Despite the fact that the generated library was very incomplete, they succeeded at isolating domains with variations of the Fc binding site that enabled novel non-Ig binding interactions with a variety of other ligands. These studies document that even a small library of variant SpA domains can be used to isolate functional domains with novel binding activities.

Figures 8A, 8B:
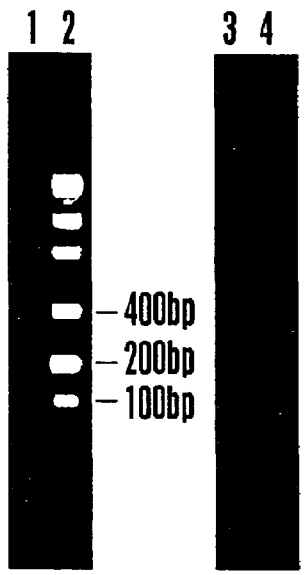
FIG. 8 is a schematic representation of the library synthesis by PCR overlap and the final primers used for preparing a variant library of synthetic SpA domain D variants for phage display. pC3H S and pC3H AS have Sfi I restriction sites incorporated into their sequences.

As discussed above, a library was designed to enable codon randomization at positions: Ala25, Gly29, Phe30, Ser33, Asp36, Asp37 and Val 44 of SpA domain D were made. These codon positions were selected based on modeling and structural analysis from the domain D-2A2 co-crystal. The structural model predicted the need for different contacts between a domain variant and a VHII clan encoded Ig. Oligonucleotides (Table V) were synthesized and purified using HPSF® by MWG-Biotech. To construct the library (strategy depicted in FIG. 8), about 100 ng of oligonucleotides, DomD Helix 1 AS and DomD Helix 2 S, were mixed with 60 pmol of primers *Helix* 1 S and *Helix* 2 AS in a PCR mix (1× PCR buffer, 20 mM dNTPs, 2.5 U Taq DNA polymerase made up to a total volume of 100 μl with dH$_2$O). For amplification, 30 temperature cycles (95° C., 30 sec; 56° C., 45 sec; 72° C., 90 sec) were run in a Perkin-Elmer GeneAmp® PCR system 9700. The amplified fragments were subsequently analyzed and purified from standard 2% agarose gel electrophoresis, using Qiaex II Kit agarose gel purification (Qiagen). In a second amplification reaction, 100 ng of the product of the Helix½ amplimer (product shown in FIG. 9, Panel A, lane 1) and the DomD Helix 3 S oligonucleotide were mixed with 60 pmol of primers pC3H S and pC3H AS with other components of the amplification buffer. This resulting product was analyzed, and then purified, as described above. The resulting full length product of 237 bp (product shown in FIG. 9, Panel B, lane 4) therefore includes a library of genes that represent variation of the SpA domain D, and also incorporates specific flanking SfiI sites for cloning into the pCOMB3H vector.

To clone the degenerate library, about 8 μg of the amplimer product was restriction digested with 388 U of Sfi I (New England Biolabs) in 200 μl of compatible buffer, overlaid with mineral oil, and incubated for 5 hrs at 50° C. The product of the desired size was gel purified on a 2% TAE agarose gel and then isolated by electroelution. hereafter, 1 μg of the prepared domain library was combined with 3 μg of previously prepared Sfi I digested pComb3H and ligated using 15 Weiss units of T4 DNA ligase overnight at 4° C. The ligation mix was heat inactivated at 65° C. for 10 minutes and ethanol precipitated and redissolved in 15 μl of sterile dH$_2$O. Pilot bacterial transformations have been performed to establish transformation frequency. DNA sequence determinations have demonstrated that individual colonies contain the pCOMB3H vector with cloned genes for variations of SpA domains with many unnatural sequence variations at the predicted codons that had been selected for randomization.

Example 13

Selection from Phage-Display Domain D-Based Libraries

Variant domains with desirable binding properties will be selected using either solid phase-associated monoclonal Ig, or B-cell membrane-associated solution phase methods (see below). Based on past experience, after a single round of adding the phage-display library to coated microtiter wells, functional clones with a wide range of binding affinities will be isolated. In later rounds, panning will result in competition between clones, resulting in selection of clones with superior affinities (57).

Initial panning efforts will use human V3–23-encoded Abs or available 7183-encoded murine Abs, which are the closest to the consensus sequences of inherited clanVHIII genes in these species (33)(33). Methods for the isolation and characterization of Abs of defined binding specificity from pComb3 combinatorial libraries are well documented in recent publications (55;57;71). In each sequential round, a different unmutated clanVHIII-encoded Ig will be employed so that L chain or CH-associated determinants, or even CDR-associated determinants are not retained. Based on the initial success herein, adapted selection strategies that may include integrated positive/negative selection (e.g. including Ig with unrelated VH regions in the block, to remove domains with undesirable activities) will be used.

Example 14

Bacterial Expression and Creation of Multivalent Forms for Subsequent Analysis To create multivalent forms of the mutant domains, a proven strategy for the creation of multimers will be followed. To create concatamers, the gene for a monomer domain is amplified with oligonucleotide primers that incorporate an upstream NheI site and the original primer creating the downstream SpeI and HindIII restriction sites (56) for transfer into the pRSETB (Invitrogen) expression vector. To create dimeric domains separated by a flexible linker, an additional domain is amplified from the monomer domain using a sense oligonucleotide that incorporates a 5' NheI site followed by extra codons upstream of the domain sequence and the original antisense oligonucleotide. The monomer containing pRSET-monomer plasmid is prepared by SpeI and HindIII digestions and purified, and the special PCR product is digested with the NheI and HindIII enzymes and purified. The overhangs created by the SpeI and NheI enzymes are complementary, and these sites are destroyed following ligation. To create the four-domain product, the process is repeated two additional times to add domains. Proteins of a greater number of domains are created by reiteration of these methods, thereby enabling generation of binding proteins with higher avidity and greater biologic activities.

TABLE I

Bonds involved in the SpA domain D-2A32 Fab interaction

| VH position | Salt Links | H bonds | Van der Waals |
|---|---|---|---|
| FW1 | | | |
| Gly H15* | | Gln 26 | Leu 51 |
| B strand Ser H17 | | | Gln 26 |
| | | | Gln 29 |
| Arg H19 | Asp 36 | | Gln 32 |
| FW3 | | | |
| C" strand Lys H57 | | Asp 36 | Asp 37 |
| Tyr H59 | | Asp 37 | Gln 40 |
| | | | Asp 37 |
| Lys H63 | | | Gln 40 |
| | | | Asn 43 |
| Gly H65* | | | Asn 43 |
| | | | Val 44 |
| | | | Glu 47 |
| Arg H66* | | | Glu 47 |
| D strand Thr H68 | | | Ser 33 |
| | | | Val 44 |
| | | | Asp 36 |
| Ile H69 | | | Asp 36 |
| Ser H70 | | | Asp 36 |
| E strand Gln H81 | | | Gln 32 |
| | | | Gly 29 |
| | | | Ser 33 |
| | | | Asp 36 |
| Asn H82a* | | Ser 33 | Gly 29 |
| | | | Phe 30 |

*Four of these $V_H$ residues are in inter-strand (but non-CDR) portions of the VH region.

TABLE II

Intrinsic Ig binding properties of recombinant SpA variants

| | Potential valency (number of domains) | Fab-binding Activity $IC_{50}$ | Fcγ-binding Activity $IC_{50}$ |
|---|---|---|---|
| SpA (native) | 5 | $2 \times 10^{(-6)}$ M | $4 \times 10^{(-7)}$ M |
| MSPA | 5 | $10^{(-5)}$ M | ND |
| DimDomD' | 2 | $5 \times 10^{(-3)}$ M | ND |
| TetmDomD' | 4 | $5 \times 10^{(-3)}$ M | ND |
| Domain D (wildtype) | 1 | $10^{(-2)}$ M | $2 \times 10^{(-4)}$ M |

$IC_{50}$ is the concentration required to inhibit 50% of the binding activity for the protein coated onto the microtiter well.
ND: Not detectable

TABLE III

Conservation or diversity at VH contact sites for a SpA domain D binding to different VH clans.

| Domain D residues | VH Contact | 2A2 Fab-Domain D Binding NCS1 (VH) | 2A2 Fab-Domain D Binding NCS2 (VH) |
|---|---|---|---|
| Gln 26 | Gly 15 | 1 VDW<br>1 H bond<br>1 VDW | 2 VDW<br>1 H bond |
| Gly 29 | Ser 17 | | 1 VDW |
| | Gln 81 | 4 VDW | 3 VDW |
| | Asn 82a | 5 VDW | 4 VDW |
| Phe 30 | Asn 82a | 4 VDW | 1 VDW |
| Gln 32 | Arg 19 | 4 VDW | 2 VDW |
| | Gln 81 | 2 VDW | 3 VDW |
| Ser 33 | Thr 68 | 1 short VDW | 4 VDW |
| | Gln 81 | 2 VDW | 2 VDW |
| | Asn 82a | 1 VDW<br>1 H bond | 1 H bond |
| Asp 36 | Arg 19 | 1 VDW<br>1 Salt link | 2 VDW<br>1 Salt link |
| | Lys 57 | 1 H bond<br>1 VDW | 1 H bond |
| | Thr 68 | 2 VDW | 5 VDW |
| | Ile 69 | | 1 VDW |
| | Ser 70 | 6 VDW | 6 VDW |
| | Gln 81 | 1 VDW | 1 VDW |
| Asp 37 | Lys 57 | 2 VDW | 4 VDW |
| | Tyr 59 | 2 VDW<br>1 H bond | 3 VDW<br>1 H bond |
| | Thr 68 | 3 VDW | none |
| Gln 40 | Tyr 59 | 3 VDW | 6 VDW |
| | Lys 63 | | 2 VDW |
| Asn 43 | Lys 63 | | 2 VDW |
| | Gly 65 | 1 VDW | 2 VDW |
| Val 44 | Gly 65 | 2 VDW | 2 VDW |

TABLE III-continued

Conservation or diversity at VH contact sites for a SpA domain D binding to different VH clans.

| Domain D residues | VH Contact | 2A2 Fab-Domain D Binding NCS1 (VH) | 2A2 Fab-Domain D Binding NCS2 (VH) |
|---|---|---|---|
| Glu 47 | Gly 65 | 3 VDW | 3 VDW |
| | Arg 66 | 3 VDW | 6 VDW |

VDW: Van der Waals forces.
H: hydrogen bonds

TABLE IV

Amino acid contact residues in Clan VHIII that differ from the corresponding position is Clan VHI and Clan VHII Ig.

| | Differences to VH3 | |
|---|---|---|
| | Contact Results | |
| Clan VHIII (2A2) | Clan VHI | Clan VHII (10) |
| Gly 15 | G | S_T |
| Ser 17 | S | T |
| Gln 81 | EQ | K_Q |
| Asn 82a | S_R | S_N |
| Arg 19 | R | S |
| Thr 68 | T | T |
| Lys 57 | T | Tn |
| Ile 69 | MI | MI_F |
| Ser 70 | T_S | S_N |
| Tyr 59 | Y | Y |
| Lys 63 | Q | K_T |
| Gly 65 | G | S |
| Arg 66 | R | R |

Underlined residues in Clan VHI or VHIII differ from VHIII.
Single letter code for amino acid residues used.
Small case letters connote less common variations.

TABLE V

Sequences of oligonucleotides used in the construction of the randomized Domain D library.

| Name | Sequence [5'->3'] |
|---|---|
| DomD Helix 1 AS | CGT TTA AGT TAG GCA TGT TGT CGA TTT CAT AGA AGG CGC TTT GTT GAT CTT TGT TGA AGT TGT TTT GTT GCG CAT CAG CGG CCG CC |
| DomD Helix 2 S | AC AAC ATG CCT AAC TTA AAC GAA NNK CAA CGT AAC NNK NNK GCA CAG NNK CTG AAA NNK NNK CCA AGC CAA AGC ACT AAC |

TABLE V-continued

Sequences of oligonucleotides used in the construction of the randomized Domain D library.

| Name | Sequence [5'->3'] |
|---|---|
| DomD Helix 3 S | CCA AGC CAA AGC ACT AAC NNK TTA GGT GAA GCT AAA AAA TTA AAC GAA TCT CAG GCA CCG AAA GGC CAG |
| Helix 1 S | G GCG GCC GCT GAT GCG |
| Helix 2 AS | GTT AGT GCT TTG GCT TGG |
| PC3H S | GAG GAG GAG GAG GTG GCC CAG GCG GCC GCT GAT GCG CAA C |
| PC3H AS | GAG GAG GAG GAG CTG GCC GGC CTG GCC TTT CGG TGC TTG AG |

REFERENCES CITED

Each reference listed herein below and referred to throughout this application is hereby incorporated by reference in its entirety.

1. Allman, D. M., Ferguson, S. E., and Cancro, M. P. 1992. Peripheral B cell maturation. I. Immature peripheral B cells in adults are heat-stable antigenhi and exhibit unique signaling characteristics. J. Immunol. 149:2533–2540.
2. Alting-Mees, M. A. and Short, J. M. 1993. Polycos vectors: a system for packaging filamentous phage and phagemid vectors using lambda phage packaging extracts. Gene 137:93–100.
3. Bachmann, M. F., Rohrer, U. H., Kundig, T. M., Burki, K., Hengartner, H., and Zinkernagel, R. M. 1993. The influence of antigen organization on B cell responsiveness. Science 262:1448–1451.
4. Barbas, C. F., Hu, D., Dunlop, N., Sawyer, L., Cababa, D., Hendry, R. M., Nara, P. L., and Burton, D. R. 1994. In vitro evolution of a neutralizing human antibody to human immunodeficiency virus type 1 to enhance affinity and broaden strain cross-reactivity. Proc. Natl. Acad. Sci. U.S.A. 91:3809–3813.
5. Berberian, L., Goodglick, L., Kipps, T. J., and Braun, J. 1993. Immunoglobulin $V_H3$ gene products: natural ligands for HIV gp120. Science 261:1588–1591.
6. Berberian, L., Valles-Ayoub, Y., Sun, N., Martinez-Maza, O., and Braun, J. 1991. A VH clonal deficit in human immunodeficiency virus-positive individuals reflects a B-cell maturational arrest. Blood. 78:175–179.
7. Braden, B. C., Goldman, E. R., Mariuzza, R. A., and Poljak, R. J. Anatomy of an antibody molecule: structure, kinetics, thermodynamics and mutational studies of the antilysozyme antibody D1.3. Immunol Rev 163, 45–57. 98.
8. Braisted, A. C. and Wells, J. A. 1996. Minimizing a binding domain from protein A. Proc. Natl. Acad. Sci. U.S.A. 93:5688–5692.
9. Brodeur, P. H. and Riblet, R. 1984. The immunoglobulin heavy chain variable region (Igh-V) locus in the mouse. I. One hundred Igh-V genes comprise seven families of homologous genes. Eur. J. Immunol. 14:922–930.
10. Brown, P. B., Kohler, H., and Rowley, D. A. 1975. Specific suppression of the antibody response in vitro by serum from paralyzed mice. J. Immunol. 115:419–424.
11. Chothia, C. and Lesk, A. M. 1987. Canonical structures for the hypervariable regions of immunoglobulins. J. Mol. Biol. 196:901–917.
12. Demaison, C., David, D., Fautrel, B., and Theze, J. 1996. V(H) gene-family representation in peripheral activated B cells from systemic lupus erythematosus (SLE) patients. Clin. Exp. Immunol. 104:439–445.
13. Desaymard, C., Giusti, A.M., and Scharff, M. D. 1984. Rat anti-T15 monoclonal antibodies with specificity for VH- and VH–VL epitopes. Mol. Immunol. 21:961–967.
14. Djojonegoro, B. M., Benedik, M. J., and Willson, R. C. 1994. Bacteriophage surface display for optimization of separations ligands: Display of immunoglobulin-binding protein A of Staphylococcus Aureus. Bio/Technology (N.Y). 12:169–172
15. Djojonegoro, B. M., Benedik, M. J., and Willson, R. C. 1994. Bacteriophage surface display of an immunoglobulin-binding domain of Staphylococcus aureus protein A. Biotechnology (N.Y). 12:169–172.
16. Drew, M. J. 1994. Resolution of refractory, classic thrombotic thrombocytopenic purpura after staphylococcal protein A immunoadsorption. Transfusion 34:536–538.
17. Endresen, C. 1979. The binding of protein A of immunoglobulin G and of Fab and Fc fragments. Acta. path. microbiol. scand. Sect. C: 185–189.
18. Feeney, A. J. 1990. Lack of N regions in fetal and neonatal mouse immunoglobulin V-D-J junctional sequences. J. Exp. Med. 172:1377–1390.
19. Feeney, A. J. 1991. Predominance of the prototypic T15 anti-phosphorylcholine junctional sequence in neonatal pre-B cells. J. Immunol. 147:4343–4350.
20. Fields, B. A., Malchiodi, E. L., Li, H., Ysern, X., Stauffacher, C. V., Schlievert, P. M., Karjalainen, K., and Mariuzza, R. A. Crystal structure of a T-cell receptor beta-chain complexed with a superantigen [see comments]. Nature 384(6605), 188–92. 96.
21. Goodnow, C. C., Crosbie, J., Adelstein, S., Lavoie, T. B., Smoth-Gill, S. J., Brink, R. A., Pritchard, B. H., Wotherspoon, J. S., Loblay, R. H., Raphael, K. et al. 1988.

Altered immunoglobulin expression and functional silencing of self-reactive B lymphocytes in transgenic mice. Nature 334:676–682.
23. Granzow, R. and Reed, R. 1992. Interactions in the fourth dimension. Bio/Technology 10:390.
24. Hakoda, M., Hayashimoto, S., Yamanaka, H., Terai, C., Kamatani, N., and Kashiwazaki, S. 1994. Molecular basis for the interaction between human IgM and staphylococcal protein A. Clin. Immunol. Immunopathol. 72:394–401.
25. Hillson, J. L., Karr, N. S., Oppliger, I. R., Mannik, M., and Sasso, E. H. 1993. The structural basis of germline-encoded $V_H3$ immunoglobulin binding to staphylococcal protein A. J. Exp. Med. 178:331–336.
26. Ibrahim, S., Seppala, I., and Makela, O. 1993. V-region-mediated binding of human Ig by protein A. J. Immunol. 151:3597–3603.
27. Ibrahim, S., Seppala, I. J., Sarvas, H., and Makela, O. 1993. Proportion of protein A bindable molecules in human IgM and IgA antibodies to seven antigens. Microb. Pathog. 15:159–168.
28. Inganas, M. 1981. Comparison of mechanisms of interaction between protein A from *Staphylococcus aureus* and human monoclonal IgG, IgA and IgM in relation to the classical Fc gamma and the alternative F(ab')2 epsilon protein A interactions. Scand. J. Immunol. 13:343–352.
29. Ito, W., Ishiguro, H., and Kurosawa, Y. 1991. A general method for introducing a series of mutations into cloned DNA using the polymerase chain reaction. Gene 102: 67–70.
30. Jansson, B., Uhlen, M., and Nygren, P. A. 1998. All individual domains of staphylococcal protein A show Fab binding. FEMS. Immunol. Med. Microbiol. 20:69–78.
31. Kabat, E. A., Wu, T. T., and Bilofsky, H. Unusual distributions of amino acids in complementarity-determining (hypervariable) segments of heavy and light chains of immunoglobulins and their possible roles in specificity of antibody-combining sites. J Biol Chem 252(19), 6609–16. 77.
32. Kavaler, J., Caton, A. J., Staudt, L. M., and Gerhard, W. 1991. A B cell population that dominates the primary response to influenza virus hemagglutinin does not participate in the memory response. Eur. J. Immunol. 21:2687–2695.
33. Kirkham, P. M., Mortari, F., Newton, J. A., and Schroeder, H. W. J. 1992. Immunoglobulin VH clan and family identity predicts variable domain structure and may influence antigen binding. EMBO J. 11:603–609.
34. Kotzin, B. L., Leung, D. Y., Kappler, J., and Marrack, P. Superantigens and their potential role in human disease. Adv Immunol 54, 99–166. 93.
35. Kozlowski, L. M., Kunning, S. R., Zheng, Y., Wheatley, L. M., and Levinson, A. I. 1995. *Staphylococcus aureus* Cowan I–induced human immunoglobin responses: Preferential IgM rheumatoid factor production and $V_H3$ mRNA expression by protein A-binding B cells. J. Clin. Immunol. 15:145–151.
36. Krishnan, M. R., Jou, N. T., and Marion, T. N. 1996. Correlation between the amino acid position of arginine in VH-CDR3 and specificity for native DNA among autoimmune antibodies. J. Immunol. 157:2430–2439.
37. Kristiansen, S. V., Pascual, V., and Lipsky, P. E. 1994. Staphylococcal protein A induces biased production of Ig by $V_H$-expressing B lymphocytes. J. Immunol. 153: 2974–2984.
38. Kushwaha, A., Chowdhury, P. S., Arora, K., Abrol, S., and Chaudhary, V. K. 1994. Construction and characterization of M13 bacteriophages displaying functional IgG-binding domains of staphylococcal protein A. Gene 151: 45–51.
39. Li, H., Liera, A., Tsuchiya, D., Leder, L., Ysern, X., Schlievert, P. M., Karjalainen, K., and Mariuzza, R. A. Three-dimensional structure of the complex between a T cell receptor beta chain and the superantigen staphylococcal enterotoxin B. Immunity 9(6), 807–16. 98.
40. Li, Y. S., Hayakawa, K., and Hardy, R.R. 1993. The regulated expression of B lineage associated genes during B cell differentiation in bone marrow and fetal liver. J. Exp. Med. 178:951–960.
41. Linton, P. J., Lo, D., Lai, L., Thorbecke, G. J., and Klinman, N. R. 1992. Among naive precursor subpopulations only progenitors of memory B cells originate germinal centers. Eur. J. Immunol. 22:1293–1297.
42. MacCallum, R. M., Martin, A. C., and Thornton, J. M. Antibody-antigen interactions: contact analysis and binding site topography. J Mol Biol 262(5), 732–45. 96.
43. Matsuda, F., Shin, E. K., Nagaoka, H., Matsumura, R., Haino, M., Fukita, Y., Taka-ishi, S., Imai, T., Riley, J. H., Anand, R. et al. 1993. Structure and physical map of 64 variable segments in the 3' 0.8 megabase region of the human immunoglobulin heavy-chain locus. Nature genetics 3:88–94.
44. Murakami, M. and Honjo, T. 1995. Involvement of B-1 cells in mucosal immunity and autoimmunity. Immunol. Today 16:534–539.
45. Newkirk, M. M., Rauch, J., Mageed, R. A., Jefferis, R., Posnett, D. N., and Silverman, G. J. 1993. Restricted immunoglobulin variable region gene usage by hybridoma rheumatoid factors from patients with systemic lupus erythematosus and rheumatoid arthritis. Mol. Immunol. 30:255–263.
46. Nguyen, A., Kavaler, J., and Erickson, J. 1994. Regulation of anti-DNA B cells in nonautoimmune transgenic mice: Functional and biochemical analyses of self-tolerance. J. Cell. Biochem. 209:Suppl. 18D.
47. Nord, K., Gunneriusson, E., Ringdahl, J., Stahl, S., Uhlen, M., and Nygren, P. A. 1997. Binding proteins selected from combinatorial libraries of an alpha-helical bacterial receptor domain. Nat. Biotechnol. 15:772–777.
48. Nord, K., Nilsson, J., Nilsson, B., Uhlen, M., and Nygren, P.A. 1995. A combinatorial library of an alpha-helical bacterial receptor domain. Protein. Eng. 8:601–608.
49. Padlan, E. A., Abergel, C., and Tipper, J. P. Identification of specificity-determining residues in antibodies. FASEB J 9(1), 133–9. 95.
50. Patten, P. A., Rock, E. P., Sonoda, T., Fazekas de St. Groth, B., Jorgensen, J. L., and Davis, M. M. Transfer of putative complementarity-determining region loops of T cell receptor V domains confers toxin reactivity but not peptide/MHC specificity. J Immunol 150(6), 2281–94. 93.
51. Pontzer, C. H., Irwin, M. J., Gascoigne, N. R., and Johnson, H. M. 1992. T-cell antigen receptor binding sites for the microbial superantigen staphylococcal enterotoxin A. Proc. Natl. Acad. Sci. U.S.A. 89:7727–7731.
52. Pullen, A. M., Bill, J., Kubo, R. T., Marrack, P., and Kappler, J. W. 1991. Analysis of the interaction site for the self superantigen M1s–1a on T cell receptor V beta. J. Exp. Med. 173:1183–1192.
53. Randen, I., Potter, K. N., Li, Y., Thompson, K. M., Pascual, V., Forre, O., Natvig, J. B., and Capra, J. D. 1993. Complementarity-determining region 2 is implicated in the binding of staphylococcal protein A to human immunoglobulin VHIII variable regions. Eur. J. Immunol. 23:2682–2686.

54. Riblet, R., Blomberg, B., Weigert, M., Lieberman, R., Taylor, B. A., and Potter, M. 1975. Genetics of mouse antibodies. I. Linkage of the dextran response locus, VH-DEX, to allotype. Eur. J. Immunol. 5:775–777.

55. Roben, P., Barbas, S. M., Sandoval, L., Lecerf, J. M., Stollar, B. D., Solomon, A., and Silverman, G. J. 1996. Repertoire cloning of lupus anti-DNA autoantibodies. J. Clin. Invest. 98:2827–2837.

56. Roben, P., Salem, A., and Silverman, G. J. 1995. $V_H3$ antibodies bind domain D of staphylococcal protein A. J. Immunol. 154:6437–6446.

57. Sasano, M., Burton, D. R., and Silverman, G. J. 1993. Molecular selection of human antibodies with an unconventional bacterial B cell superantigen. J. Immunol. 151:5822–5839.

58. Sasso, E. H., Silverman, G. J., and Mannik, M. 1989. Human IgM molecules that bind staphylococcal protein A contain VHIII H chains. J. Immunol. 142:2778–2783.

59. Sasso, E. H., Silverman, G. J., and Mannik, M. 1991. Human IgA and IgG F(ab')2 that bind to staphylococcal protein A belong to the VHIII subgroup. J. Immunol. 147:1877–1883.

60. Seppala, I., Kaartinen, M., Ibrahim, S., and Makela, 0. 1990. Mouse Ig coded by VH families S107 or J606 bind to protein A. J. Immunol. 145:2989–2993.

61. Sheriff, S., Silverton, E. W., Padlan, E. A., Cohen, G. H., Smith-Gill, S. J., Finzel, B. C., and Davies, D. R. (1987) Three-dimensional structure of an antibody-antigen complex. Proc Natl Acad Sci USA 84(22), 8075–9.

62. Siegel, D. L., Chang, T. Y., Russell, S. L., and Bunya, V. Y. 1997. Isolation of cell surface-specific human monoclonal antibodies using phage display and magnetically-activated cell sorting: applications in immunohematology. J. Immunol. Methods 206:73–85.

63. Silberstein, L. E., Jefferies, L. C., Goldman, J., Friedman, D., Moore, J. S., Nowell, P. C., Roelcke, D., Pruzanski, W., Roudier, J., and Silverman, G. J. 1991. Variable region gene analysis of pathological human autoantibodies to the related i and I red blood cell antigens. Blood. 78:2372–2386.

64. Silberstein, L. E., Jefferies, L. C., Goldman, J., Friedman, D., Moore, J. S., Nowell, P. C., Roelcke, D., Pruzanski, W., Roudier, J., and Silverman, G. J. 1991. Variable region gene analysis of pathological human autoantibodies to the. Blood. 78:2372–2386.

65. Silverman, G. J. 1992. Human antibody responses to bacterial antigens: studies of a model conventional antigen and a proposed model B cell superantigen. Int. Rev. Immunol. 9:57–78.

66. Silverman, G. J. 1994. Superantigens and the spectrum of unconventional B cell antigens. The Immunologist 2:51–57.

67. Silverman, G. J., Goni, F., Fernandez, J., Chen, P. P., Frangione, B., and Carson, D. A. 1988. Distinct patterns of heavy chain variable region subgroup use by human monoclonal autoantibodies of different specificity. J. Exp. Med. 168:2361–2366.

68. Silverman, G. J., Nayak, J. V., Warnatz, K., Cary, S., Tighe, H., and Curtiss, V. E. 1998. The dual phases of the response to neonatal exposure to a VH family-restricted staphylococcal B-cell superantigen. J. Immunol. 161:5720–5732.

69. Silverman, G. J., Pires, R., and Bouvet, J. P. 1996. An endogenous sialoprotein and a bacterial B cell superantigen compete in their VH family-specific binding interactions with human Igs. J. Immunol. 157:4496–4502.

71. Silverman, G. J., Roben, P., Bouvet, J.-P., and Sasano, M. 1995. Superantigen properties of a human sialoprotein involved in gut-associated immunity. J. Clin. Invest. 96:417–426.

73. Silverman, G. J., Sasano, M., and Wormsley, S. B. 1993. Age-associated changes in binding of human B lymphocytes to a $V_H3$-restricted unconventional bacterial antigen. J. Immunol. 151:5840–5855.

74. Silverman, G. J., Sasano, M., and Wormsley, S. B. 1993. The variable-region specificity of bacterial Fab-binding proteins: The search for B cell superantigens. Immunomethods 2:17–23.

75. Silverman, G. J., Schrohenloher, R. E., Accavitti, M. A., Koopman, W. J., and Carson, D. A. 1990. Structural characterization of the second major cross-reactive idiotype group of human rheumatoid factors. Association with the VH4 gene family. Arthritis Rheum. 33:1347–1360.

76. Smith, G. P. 1985. Filamentous fusion phage: novel expression vectors that display cloned antigens on the virion surface. Science 228:1315–1317.

77. Starovasnik, M. A., Braisted, A. C., and Wells, J. A. 1997. Structural mimicry of a native protein by a minimized binding domain. Proc. Natl. Acad. Sci. U.S.A. 94:10080–10085.

78. ten Boekel, E., Melchers, F., and Rolink, A. G. 1998. Precursor B cells showing H chain allelic inclusion display allelic exclusion at the level of pre-B cell receptor surface expression. Immunity. 8:199–207.

79. Tighe, H., Warnatz, K., Brinson, D., and Corr, M. 1997. Peripheral deletion of rheumatoid factor B cells after abortive activation by IgG. Proc. Natl. Acad. Sci. U.S.A. 94:646–651.

80. Tomlinson, I. M., Cook, G. P., Carter, N. P., Elaswarapu, R., Smith, S., Walter, G., Buluwela, L., Rabbitts, T. H., and Winter, G. 1994. Human immunoglobulin VH and D segments on chromosomes 15q11.2 and 16 p11.2. Hum. Mol. Genet. 3:853–860.

81. Tomlinson, I. M., Walter, G., Marks, J. D., Llewelyn, M. B., and Winter, G. 1992. The repertoire of human germline VH sequences reveals about fifty groups of VH segments with different hypervariable loops. J. Mol. Biol. 227:776–798.

82. Warner, G. L., Davies, S., and Scott, D. W. 1989. Cholera toxin-sensitive and insensitive signaling via surface Ig. J. Immunol. 143:458–463.

83. Webb, S. R. and Gascoigne, N. R. T-cell activation by superantigens. Curr Opin Immunol 6(3), 467–75. 94.

84. White, J., Herman, A., Pullen, A. M., Kubo, R., Kappler, J. W., and Marrack, P. 1989. The V beta-specific superantigen staphylococcal enterotoxin B: stimulation of mature T cells and clonal deletion in neonatal mice. Cell 56:27–35.

85. White, J., Pullen, A., Choi, K., Marrack, P., and Kappler, J. W. 1993. Antigen recognition properties of mutant V beta 3+ T cell receptors are consistent with an immunoglobulin-like structure for the receptor. J. Exp. Med. 177:119–125.

86. Whitmore, A. C., Prowse, D. M., Haughton, G., and Arnold, L. W. 1991. Ig isotype switching in B lymphocytes. The effect of T cell-derived interleukins, cytokines, cholera toxin, and antigen on isotype switch frequency of a cloned B cell lymphoma. Int. Immunol. 3:95–103.

87. Wiesenhutter, C. W., Irish, B. L., and Bertram, J. H. 1994. Treatment of patients with refractory rheumatoid arthritis with extracorporeal protein A immunoadsorption columns: a pilot trial. J. Rheumatol. 21:804–812.
88. Wilson, I. A. and Stanfield, R. L. (1994) Antibody-antigen interactions: new structures and new conformational changes. Curr Opin Struct Biol 4(6), 857–67.
89. Wilson, I. A. Stanfield R. L. (1993) Antibody-antigen interactions. Current Biology 4, 857–867.
90. Young, W. W., Tamura, Y., Wolock, D. M., and Fox, J. W. 1984. Staphylococcal protein A binding to the Fab of mouse monoclonal antibodies. J. Immunol. 133:3163–3166.
91. Zhang, M., Majid, A., Bardwell, P., Vee, C., and Davidson, A. (1998) Rheumatoid factor specificity of a $V_H3$-encoded antibody is dependent on the heavy chain CDR3 region and is independent of protein A binding. J Immunol 161(5), 2284–9.

What is claimed is:

1. A method for preferentially reducing the number, or arresting the activation, of B lymphocytes that express immunoglobulin Fab sequences from variable heavy chain III genes ($V_H3$ Ig-Fab expressing lymphocytes) in an individual in need of such treatment, the method comprising administering a pharmaceutical composition consisting essentially of isolated monomeric Staphylococcal protein A (SpA) having more than one Fc binding domain therein to the individual in an amount sufficient to cause such reduction or arrest.

2. The method according to claim 1, wherein the $V_H3$ Ig-Fab expressing lymphocytes are neoplastic B cells.

3. The method according to claim 1, wherein the $V_H3$ Ig-Fab expressing lymphocytes are autoreactive B cells.

4. The method according to claim 1, wherein the number of $V_H3$ expressing lymphocytes is reduced, and such reduction is achieved at a level of at least 80%, compared to the number of such lymphocytes present prior to administration of SpA.

5. The method according to claim 1, wherein the individual is suffering from a condition selected from the group consisting of idiopathic thrombocytopenia, rheumatoid arthritis, SLE, thyroiditis, and diabetes.

6. A method for preferentially reducing the number, or arresting the activation, of B lymphocytes that express immunoglobulin Fab sequences from variable heavy chain III genes ($V_H3$ Ig-Fab expressing lymphocytes) in an individual in need of such treatment, wherein said lymphocytes express immunoglobulin Fab sequences from variable heavy chain III genes ($V_H3$ Ig-Fab expressing lymphocytes), the method comprising administering a pharmaceutical composition consisting essentially of isolated monomeric Staphylococcal protein A (SpA) having more than one Fc binding domain therein to the individual in an amount between 0.01 and 50 mg SpA protein/kg body weight, to cause such reduction or arrest.

7. The method according to claim 6, wherein the $V_H3$ Ig-Fab expressing lymphocytes are neoplastic B cells.

8. The method according to claim 6, wherein the $V_H3$ Ig-Fab expressing lymphocytes are autoreactive B cells.

9. The method according to claim 6, wherein the number of $V_H3$ expressing lymphocytes is reduced, and such reduction is achieved at a level of at least 80%, compared to the number of such lymphocytes present prior to administration of SpA.

10. The method according to claim 6, wherein the individual is suffering from idiopathic thrombocytopenia, rheumatoid arthritis, SLE, thyroiditis, or diabetes.

* * * * *